US011351169B2

(12) United States Patent
Ciallella et al.

(10) Patent No.: US 11,351,169 B2
(45) Date of Patent: Jun. 7, 2022

(54) METHODS OF TREATING DYSKINESIA AND RELATED DISORDERS

(71) Applicant: Melior Pharmaceuticals II, LLC, Exton, PA (US)

(72) Inventors: John Ciallella, Exton, PA (US); John Gruner, Exton, PA (US); Andrew G. Reaume, Exton, PA (US); Michael S. Saporito, Exton, PA (US)

(73) Assignee: Melior Pharmaceuticals II, LLC, Exton, PA (US)

( * ) Notice: Subject to any disclaimer, the term of this patent is extended or adjusted under 35 U.S.C. 154(b) by 0 days.

(21) Appl. No.: 16/214,355

(22) Filed: Dec. 10, 2018

(65) Prior Publication Data

US 2019/0328736 A1    Oct. 31, 2019

Related U.S. Application Data

(60) Continuation of application No. 15/195,699, filed on Jun. 28, 2016, now Pat. No. 10,188,651, which is a division of application No. 14/702,242, filed on May 1, 2015, now Pat. No. 9,402,830, which is a continuation of application No. 14/472,794, filed on Aug. 29, 2014, now Pat. No. 9,051,312, which is a continuation of application No. PCT/US2014/029827, filed on Mar. 14, 2014.

(60) Provisional application No. 61/786,714, filed on Mar. 15, 2013.

(51) Int. Cl.
| | |
|---|---|
| *A61K 9/00* | (2006.01) |
| *A61K 31/198* | (2006.01) |
| *A61K 31/501* | (2006.01) |
| *A61K 31/506* | (2006.01) |
| *C07D 271/04* | (2006.01) |
| *C07D 413/12* | (2006.01) |
| *A61K 31/4245* | (2006.01) |
| *A61K 31/4439* | (2006.01) |

(52) U.S. Cl.
CPC .......... *A61K 31/506* (2013.01); *A61K 9/0053* (2013.01); *A61K 31/198* (2013.01); *A61K 31/4245* (2013.01); *A61K 31/4439* (2013.01); *A61K 31/501* (2013.01); *C07D 271/04* (2013.01); *C07D 413/12* (2013.01); *Y02A 50/30* (2018.01)

(58) Field of Classification Search
CPC ............ A61K 31/4245; A61K 2300/00; A61K 31/501; A61K 31/4439; A61K 31/198
See application file for complete search history.

(56) References Cited

U.S. PATENT DOCUMENTS

| | | | |
|---|---|---|---|
| 3,312,690 A | 4/1967 | Masuda et al. | |
| 4,446,322 A | 5/1984 | Stein | |
| 5,179,206 A | 1/1993 | Kujath et al. | |
| 2008/0319030 A1 | 12/2008 | Chen et al. | |
| 2011/0207718 A1* | 8/2011 | Bird ........................ | A61P 25/28 514/217 |
| 2011/0288137 A1 | 11/2011 | Chen et al. | |
| 2012/0264698 A1 | 10/2012 | Chen et al. | |
| 2014/0142140 A1* | 5/2014 | Bird ................... | A61K 31/4192 514/319 |

FOREIGN PATENT DOCUMENTS

| | | |
|---|---|---|
| CA | 1097659 | 3/1981 |
| WO | 8100567 | 3/1981 |
| WO | 8201184 | 4/1982 |
| WO | 8201187 | 4/1982 |
| WO | 9318767 | 9/1993 |
| WO | 2008112968 | 9/2008 |
| WO | 2010015029 | 2/2010 |
| WO | 2011069051 | 6/2011 |

OTHER PUBLICATIONS

Afanas'ev et al., "Effects of amphetamine and syndocarb on dopamine release and free radical generation in rat striatum", Pharmacol Biochem Behav, 2001, 69(3-4):653-658.
Al'Tshuler, "Comparative Molecular Model Estimation of the Affinity of Phenylethylamines to the Binding Sites of Membrane Transporters", Pharm Chem J, 2005, 39(4), pp. 169-175.
Anderzhanova et al., "Effect of d-amphetamine and syndocarb on the extracellular level of dopamine, 3,4-dihydroxyphenylacetic acid, and hydroxyl radicals generation in rat striatu", Ann NY Acad Sci, 2000, 914:137-145.
Anderzhanova et al., "Effects of syndocarb and D-amphetamine on the extracellular levels of amino acids in the rat caudate-putamen", Eur J Pharmacol, 2001, 428(1):87-95.
Bashkalova et al., "Neurochemical changes and neurotoxic effects of an acute treatment with syndocarb, a novel psychostimulant: comparison with D-amphetamine", Ann NY Acad Sci, 2002, 965:180-192.
CAS RN 1294450-39-7, STN Entry Date May 13, 2011.
CAS RN 1301742-33-5, STN Entry Date May 27, 2011.
CAS RN 157856-28-5, STN Entry Date Sep. 23, 1994.
CAS RN 475157-69-8, STN Entry Date Dec. 5, 2002.
CAS RN 496923-30-9, STN Entry Date Mar. 5, 2003.
CAS RN 755705-34-1, STN Entry Date Oct. 1, 2004.
CAS RN 756771-00-3, STN Entry Date Oct. 4, 2004.
CAS RN 774130-89-1, STN Entry Date Nov. 2, 2004.
CAS RN 785001-95-8, STN Entry Date Nov. 19, 2004.

(Continued)

*Primary Examiner* — Shirley V Gembeh

(74) *Attorney, Agent, or Firm* — Stradley Ronon Stevens & Young, LLP

(57) ABSTRACT

The present disclosure describes compounds and pharmaceutically acceptable salts thereof and compositions and formulations comprising the same that are useful in methods of treating dyskinesia or related disorders, and methods for treating dyskinesia or related disorders.

9 Claims, 7 Drawing Sheets

(56) References Cited

OTHER PUBLICATIONS

CAS RN 786594-66-9, STN Entry Date Nov. 22, 2004.
CAS RN 791015-23-1, STN Entry Date Nov. 30, 2004.
CAS RN 793610-92-1, STN Entry Date Dec. 6, 2004.
Claassen et al. "Sleep disturbances in Parkinson's disease patients and management options", Nat. Sci Sleep, 2011, 3:125-13.
Cody, "Precursor medications as a source of methamphetamine and/or amphetamine positive drug testing results", J Occup Environ Med, 2002, 44(5):435-450.
Database accession No. 1976:38935; Temkov, I. et al., "Syndocarb, a new psychostimulant drug", XP002764837.
Erdo et al., "Inhibition of dopamine uptake by a new psychostimulant mesocarb (Syndocarb)", Pol J Pharmacol Pharm, 1981, 33(2):141-147.
Flood et al., "The effects of d-amphetamine, methylphenidate, syndocarb, and caffeine on prepulse inhibition of the startle reflex in DBA/2 mice", Psychopharmacology (Berl), 2010, 211(3):325-336.
Gainetdinov et al., "Effects of a psychostimulant drug syndocarb on rat brain dopaminergic transmission in vivo", Eur J Pharmacol, 1997, 340(1):63-68.
Gomez, C., et al., "Identification of free and conjugated metabolites of mesocarb in human urine by LC-MS/MS", Analytical and Bioanalytical Chemistry, 2010, 397(7), pp. 2903-2916.
Gruner et al., "Characterization of pharmacological and wake-promoting properties of the dopaminergic stimulant syndocarb in rats", J Pharmacol Exp Ther, 2011, 337(2):380-390.
Hauser et al., "Randomized trial of the triple monoamine reuptake inhibitor NS 2330 (tesofensine) in early Parkinson's disease", Mov Disord, 2007, 22(3):359-365.
Lee, BCMJ, 2001 43(4):206-209.
Lokk, "Daytime sleepiness in elderly Parkinson's disease patients and treatment with the psychostimulant modafinil: a preliminary study", Neuropsychiatr Dis Treat, 2010, 6:93-97.
Olovyanishnikova, Z., et al., "Electrophilic Substitution in a Number of N-exo-carbamoyl Derivatives of Sydnoneimines", Chemistry of Heterocyclic Compounds, 1975, 9, pp. 1041-1046.
Olovyanishnikova, Z., et al., "Synthesis and Psychostimulatory Activity of Sydnocarb Analogs", Pharmaceutical Chemistry Journal, 1987, 21(11), pp. 756-759.
Olson et al., Brain, 2000, 123:331-339.
Parshin, V., et al., "Synthesis and Pharmacological Properties of Sydnocarb Analogs with Hydroxyl and Carboxyl Groups", Pharmaceutical Chemistry Journal, 1981, 15(5), pp. 333-337.
Racsol et al., "Tesofinsine (NS 2330), a monoamine reuptake inhibitor, in patients with advanced Parkinson's disease and motor fluctuations: the ADVANS Study", Arch Neurol, 2008, 65(5):577-583.
Salas et at., Letters to the Editor/Sleep Medicine, 2009, 10:396-397.
The Stanford Center for Sleep Sciences and Medicine, 2016.
Vahermo, M., et al., "Synthesis and Characterization of Hydroxylated Mesocarb Metabolites for Doping Control", Archiv der Pharmazie, 2009, 342(4), pp. 201-209.
Vinar et al., "A survey of psychotropic medications not available in the United States", Neuropsychopharmacology, 1991, 5(4):201-217.
Witkin et al., "Behavioral, topix, and neurochemical effects of syndocarb, a novel psychomotor stimulant: comparisons with methamphetamine", J Pharmacol Exp Ther, 1999, 288(3):1298-1310.
Temkov et al., "Study of a New Psychostimulant Sydnocarb", Nuerology, Psychiatry and Neurosurgery, 14, 1975, 179-183 (translated).

* cited by examiner

A = Vehicle + Vehicle    B = Vehicle + L-dopa    C = Sydnocarb (10 mg/kg) + L-dopa 1 = Untreated  2 = MPTP
3 = Sydnocarb (3 mg/kg)  4 = Sydnocarb (10 mg/kg)
5 = Sydnocarb (30 mg/kg)  6 = Tesofensine (1 mg/kg)

1 = Vehicle; 2 = Sydnocarb (10 mg/kg); 3 = Sydnocarb (30 mg/kg); 4 = Amantadine (40 mg/kg)

1 = Vehicle; 2 = Sydnocarb (10 mg/kg)

□ = Vehicle (L-dopa); ■ = L-dopa + Sydnocarb (3 mg/kg); ▲ = L-dopa + Sydnocarb (10 mg/kg)

METHODS OF TREATING DYSKINESIA AND RELATED DISORDERS

FIELD

The present disclosure describes compounds, compositions, and formulations comprising therapeutically or prophylactically active compounds or pharmaceutically acceptable salts thereof, for treating and/or preventing dyskinesias or other disorders, and methods for treating dyskinesia or other disorders.

BACKGROUND

Sydnocarb (i.e., 3-(β-phenylisopropyl)-N-phenylcarbamoylsydnonimine), also known as mesocarb, is a psychomotor stimulant. In Russia, sydnocarb has been used for over 30 years to treat a variety of neuropsychiatric comorbidities such as asthenia, apathy, and adynamia (Anokhina et al., Zh Nevropatol Psikhiatr Im S S Korsakova, 1974, 74, 594-602; Vinar et al., Neuropsychopharmacology, 1991, 5, 201-217; and Cody, J. Occup. Environ. Med., 2002, 44, 435-450). Although mostly anecdotal, evidence may suggest that sydnocarb increases endurance during heavy physical activity and resistance to environmental stressors such as hypothermia, low gravity, and oxygen deprivation. Sydnocarb may also have beneficial effects in treating alcohol abuse, attention deficit hyperactivity disorder (ADHD), and cognitive impairment (Rudenko et al., Agressologie, 1979, 20, 265-270; Vinar et al., supra; Cody, supra).

Although sydnocarb-induced facilitation of dopamine (DA)-mediated transmission has been well established in microdialysis studies, the exact nature of this action (i.e., DA release versus DA transporter (DAT) inhibition) is not clear (Gainetdinov et al., Eur. J. Pharmacol., 1997, 340, 53-58; Afanas'ev et al., Pharmacol. Biochem. Behav., 2001, 69, 653-658; Anderzhanova et al., Eur. J. Pharmacol., 2001, 428, 87-95). More recently, it has been demonstrated that sydnocarb has DAT activity and lacks the rebound hypersomnolence, characteristic of compounds that cause dopamine release (Gruner et al., J. Pharmacol. Exp. Therap., 2011, 337, 380-390). It has been reported that sydnocarb attenuates noradrenaline reuptake based on experiments in rat synaptosomes (Erdö et al., Pol. J. Pharmacol. Pharm., 1981, 33, 141-147). Sydnocarb is also metabolized to D-amphetamine (D-AMPH) in humans and animals, but the role of D-AMPH in the net in vivo effects of sydnocarb is unclear. In vivo pharmacological profiles of sydnocarb and D-AMPH largely overlap, suggesting that either sydnocarb and D-AMPH are functionally indistinguishable or the metabolite D-AMPH contributes significantly to the effects produced by sydnocarb (Gainetdinov et al., supra; Witkin et al., J. Pharmacol. Exp. Ther., 1999, 288, 1298-1310; Anderzhanova et al., Ann. NY Acad. Sci., 2000, 914, 137-145; Flood et al., Psychopharmacology, 2010, 211, 325-336). However, there are some important differences between the two drugs. Unlike D-AMPH, neither significant toxic episodes nor abuse potential have been reported with sydnocarb in humans (Mashkovskii et al., Zh Nevropatol Psikhiatr Im S S Korsakova, 1971, 71, 1704-1709; Rudenko et al., supra). Compared with D-AMPH, the stimulating effects of sydnocarb develop more gradually, last longer, and are not accompanied by pronounced euphoria, motor excitation, or peripheral sympathomimetic effects such as tachycardia and hypertension (Rudenko et al., supra). In animals, sydnocarb produces a slower and more gradual increase in extracellular DA in the rat striatum and nucleus accumbens compared with D-AMPH (Gainetdinov et al., supra; Witkin et al., supra; Anderzhanova et al., supra). Relative to D-AMPH, equimolar doses of sydnocarb produce less hyperlocomotion and stereotypy as well as smaller changes in the markers of neurotoxicity such as DA depletion, generation of reactive oxygen species, or increases in specific indices of lipid peroxidation (Gainetdinov et al., supra; Witkin et al., supra; Anderzhanova et al., supra; Afanas'ev et al., supra; Bashkatova et al., Ann. NY Acad. Sci., 2002, 965, 180-192). Furthermore, sydnocarb does not exhibit the rebound hypersomnolence seen with D-AMPH as a result of the dopamine release characteristics associated with D-AMPH (Gruner et al., supra). Several studies aimed at investigating the utility of DAT inhibitors in Parkinson's Disease have indicated very little or no utility towards this disease, especially as regards the potential utility of DAT inhibitors towards L-dopa-induced dyskinesias associated with Parkinson's Disease (Lökk, J., Neuropsych. Dis. Treat., 2010, 6, 93-97; Hauser et al., Mov. Disord., 2007, 22, 359-365; and Rascol et al., Arch Neurol., 2008, 65, 577-583).

SUMMARY

The present disclosure encompasses compounds, compositions, and formulations that may be useful in treating dyskinesia or other disorders in a mammal. In some embodiments, the mammal has or is suspected of having a dyskinesia or another disorder. In particular, the compounds, compositions, and formulations useful in treating a dyskinesia or other disorders include, but are not limited to, compounds, compositions, and formulations comprising a compound of Formulas I set forth herein.

The present disclosure provides compounds of Formula Ia-1, Formula Ia-2, Formula Ib-1, Formula Ib-2, Formula Ic-1, Formula Ic-2, Formula Id-1, or Formula Id-2:

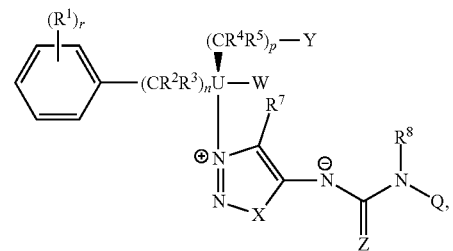

(Ia-1)

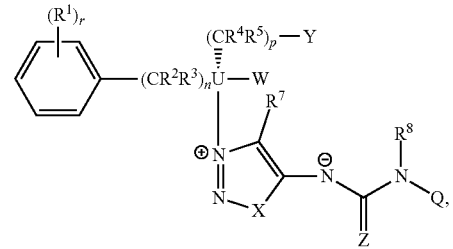

(Ia-2)

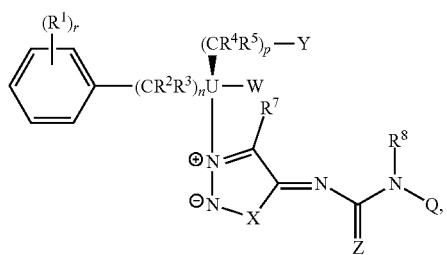
(Ib-1)

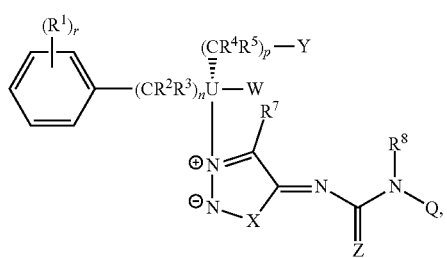
(Ib-2)

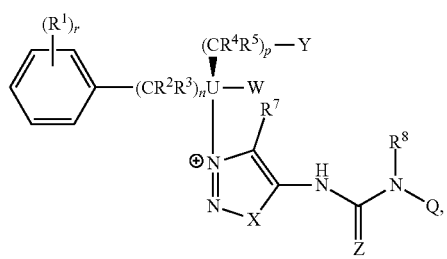
(Ic-1)

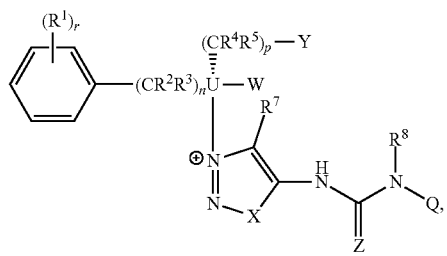
(Ic-2)

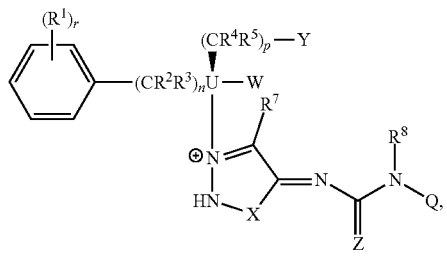
(Id-1)

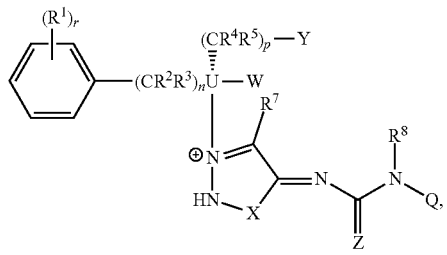
(Id-2)

or a pharmaceutically acceptable salt thereof, wherein: U is C or N; each $R^1$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —N($=$O)$_2$, —C($=$O)OH, —$NH_2$, —$CF_3$, —NH($C_1$-$C_6$alkyl), —N($C_1$-$C_6$alkyl)$_2$, —C($=$O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl, where r is 0, 1, 2, 3, 4, or 5; each $R^2$ and $R^3$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —C($=$O)OH, —$NH_2$, —$CF_3$, —NH($C_1$-$C_6$alkyl), —N($C_1$-$C_6$alkyl)$_2$, —C($=$O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, dialkylaminosulfinylalkyl, aryl, or aryl$C_1$-$C_6$alkyl, where n is 0, 1, 2, 3, or 4; each $R^4$ and $R^1$ is, independently, H, $C_1$-$C_6$alkyl, $C_2$-$C_6$alkenyl, $C_2$-$C_6$alkyl, $C_1$-$C_6$alkoxy, $C_1$-$C_6$alkylthio, —CN, —OH, —SH, halo, haloalkyl, —$NO_2$, —C($=$O)OH, —$NH_2$, —$CF_3$, —NH($C_1$-$C_6$alkyl), —N($C_1$-$C_6$alkyl)$_2$, —C($=$O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, dialkylaminosulfinylalkyl, aryl, or aryl$C_1$-$C_6$alkyl, where p is 0, 1, 2, 3, or 4; W is H or $C_1$-$C_6$alkyl; Y is H, $C_1$-$C_6$alkoxy, $C_1$-$C_6$alkylthio, —CN, —OH, —SH, halo, haloalkyl, —$NO_2$, —C($=$O)OH, —$NH_2$, —$CF_3$, —NH($C_1$-$C_6$alkyl), —N($C_1$-$C_6$alkyl)$_2$, —C($=$O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl; X is O or S; Z is O or S; $R^1$ is H or halo; Q is H, $C_1$-$C_6$alkyl, aryl, $C_1$-$C_6$alkylaryl, $C_3$-$C_6$cycloalkyl, or heteroaryl, each of which is optionally substituted with —$(R^6)_t$, where t is 0, 1, 2, 3, 4, or 5; $R^8$ is H or $C_1$-$C_6$alkyl; each $R^6$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —N($=$O)$_2$, —C($=$O)OH, —$NH_2$, —$CF_3$, —O—S($=$O)$_2$OH, —NH($C_1$-$C_6$alkyl), —N($C_1$-$C_6$alkyl)$_2$, —C($=$O)H, —C($=$O)$C_1$-$C_6$alkyl, —C($=$O)$C_1$-$C_6$alkoxy, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl.

The present disclosure also provides compositions comprising a compound of Formula Ia-1, Formula Ia-2, Formula Ib-1, Formula Ib-2, Formula Ic-1, Formula Ic-2, Formula Id-1, or Formula Id-2, or pharmaceutically acceptable salt thereof. In some embodiments, the composition further comprises another therapeutic agent which is an anti-Parkinsonian agent, an agent used to treat dyskinesias, or an agent that induces dyskinesias.

The present disclosure also provides formulations for oral administration in the form of a tablet, gel-cap, or capsule comprising from about 1 mg to about 1000 mg of a compound of Formula Ia-1, Formula Ia-2, Formula Ib-1, Formula Ib-2, Formula Ic-1, Formula Ic-2, Formula Id-1, or Formula Id-2, or pharmaceutically acceptable salt thereof. In some embodiments, the formulation further comprises another therapeutic agent chosen from an anti-Parkinsonian agent, an agent used to treat dyskinesias, or an agent that induces dyskinesias.

The present disclosure also provides methods of treating a dyskinesia or other disorders in a mammal comprising administering to the mammal in need thereof an effective amount of a compound of Formula Ia-1, Formula Ia-2, Formula Ib-1, Formula Ib-2, Formula Ic-1, Formula Ic-2, Formula Id-1, or Formula Id-2:

(Ia-1)

(Ia-2)

(Ib-1)

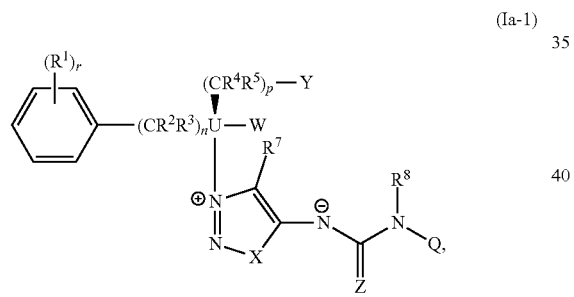

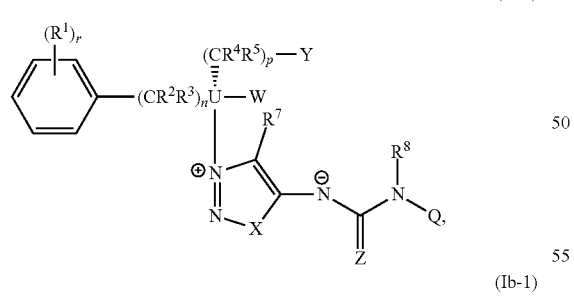

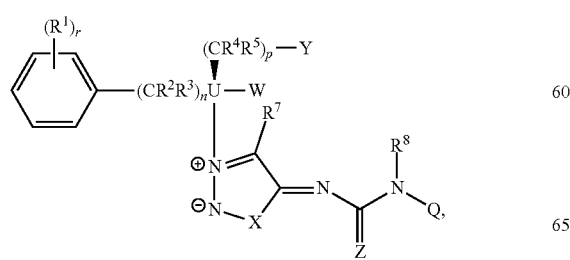

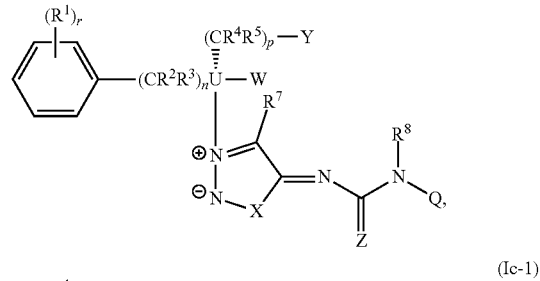

(Ib-2)

(Ic-1)

(Ic-2)

(Id-1)

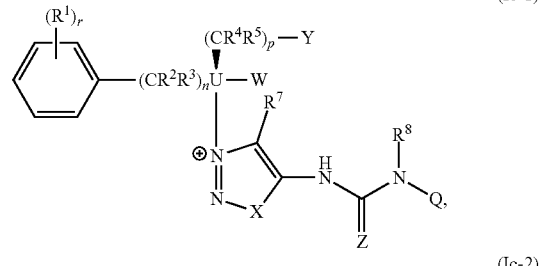

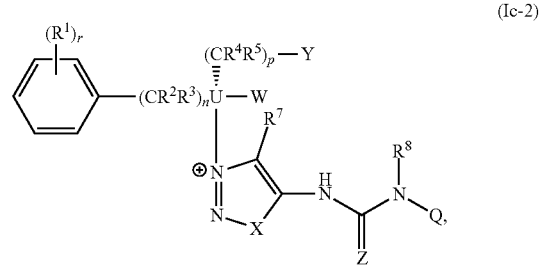

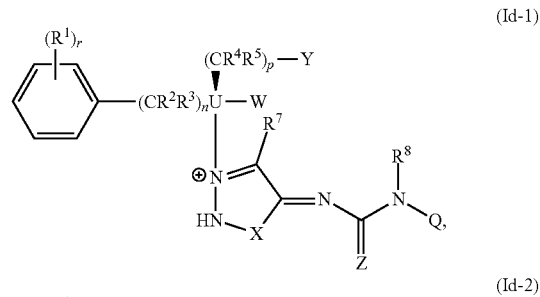

(Id-2)

or a pharmaceutically acceptable salt thereof, wherein: U is C or N; each $R^1$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —N(=O)$_2$, —C(=O)OH, —$NH_2$, —$CF_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl, where r is 0, 1, 2, 3, 4, or 5; each $R^2$ and $R^3$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —C(=O)OH, —$NH_2$, —$CF_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, dialkylaminosulfinylalkyl, aryl, or aryl$C_1$-$C_6$alkyl, where n is 0, 1, 2, 3, or 4; each $R^4$ and $R^5$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —C(=O)OH, —$NH_2$, —$CF_3$. —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonyl alkyl, dialkyl aminosulfonyl alkyl, aminosulfinylalkyl, monoalkylaminosulfinylalkyl, dialkylaminosulfinylalkyl, aryl, or aryl$C_1$-$C_6$alkyl, where p is 0, 1, 2, 3, or 4; W is H or $C_1$-$C_6$alkyl; Y is H, $C_1$-$C_6$alkoxy, $C_1$-$C_6$alkylthio, —CN, —OH, —SH, halo, haloalkyl, —$NO_2$, —C(=O)OH, —$NH_2$, —$CF_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl; X is O or S; Z is O or S; $R^7$ is H or halo; Q is H, $C_1$-$C_6$alkyl, aryl, $C_1$-$C_6$alkylaryl, $C_3$-$C_6$cycloalkyl, or heteroaryl, each of which is optionally substituted with —($R^6$)$_t$, where t is 0, 1, 2, 3, 4, or 5; $R^8$ is H or $C_1$-$C_6$alkyl; and each $R^6$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —N(=O)$_2$, —C(=O)OH, —$NH_2$, —$CF_3$, —O—S(=O)$_2$OH, —NH($C_1$-$C_6$alkyl), —N($C_1$-$C_6$alkyl)$_2$, —C(=O)H, —C(=O)$C_1$-$C_6$alkyl, —C(=O)$C_1$-$C_6$alkoxy, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl; or pharmaceutically acceptable salt thereof, wherein the other disorder is restless leg syndrome (such as drug-induced or idiopathic), a drug-induced dystonia, chorea (such as Huntington's disease, toxin-induced chorea, Sydenham's chorea, Chorea gravidarum, Wilson's disease, drug-induced chorea, and metabolic and endocrine-related choreas), a tic (such as motor, phonic, simple, complex, and Tourette syndrome), a dystonia (such as acute, generalized, focal, segmental, sexual, intermediate, psychogenic, and Acute Dystonic Reaction), Sodemytopic Parkinson's, a stereotypic movement disorder (such as movement disorder related to autism, genetic, and childhood), obsessive compulsive disorder, narcolepsy (such as cataplexy), transmissible spongiform encephalopathies (such as Creutzfeldt-Jakob disease and Kuru), neuroacanthocytosis, seizure and convulsions, athetosis (such as related to Huntington's Disease, asphyxia, neonatal jaundice, and stroke), or cerebral palsy.

In some embodiments, the dyskinesia is levodopa-induced dyskinesia, chronic or tardive dyskinesia, or orofacial dyskinesia.

The present disclosure also provides compounds of Formula Ia-1, Formula Ia-2, Formula Ib-1, Formula Ib-2, Formula Ic-1, Formula Ic-2, Formula Id-1, or Formula Id-2, or pharmaceutically acceptable salt thereof, for treating a dyskinesia (such as levodopa-induced dyskinesia, chronic or tardive dyskinesia, and orofacial dyskinesia), restless leg syndrome (such as drug-induced or idiopathic), a drug-induced dystonia, chorea (such as Huntington's disease, toxin-induced chorea, Sydenham's chorea, Chorea gravidarum, Wilson's disease, drug-induced chorea, and metabolic and endocrine-related choreas), a tic (such as motor, phonic, simple, complex, and Tourette syndrome), a dystonia (such as acute, generalized, focal, segmental, sexual, intermediate, psychogenic, and Acute Dystonic Reaction), Sodemytopic Parkinson's, a stereotypic movement disorder (such as movement disorder related to autism, genetic, and childhood), obsessive compulsive disorder, narcolepsy (such as cataplexy), transmissible spongiform encephalopathies (such as Creutzfeldt-Jakob disease and Kuru), neuroacanthocytosis, seizure and convulsions, athetosis (such as related to Huntington's Disease, asphyxia, neonatal jaundice, and stroke), or cerebral palsy.

The present disclosure also provides compounds of Formula Ia-1, Formula Ia-2, Formula Ib-1, Formula Ib-2, Formula Ic-1, Formula Ic-2, Formula Id-1, or Formula Id-2, or pharmaceutically acceptable salt thereof, for use in the manufacture of a medicament for treating a dyskinesia (such as levodopa-induced dyskinesia, chronic or tardive dyskinesia, and orofacial dyskinesia), restless leg syndrome (such as drug-induced or idiopathic), a drug-induced dystonia, chorea (such as Huntington's disease, toxin-induced chorea, Sydenham's chorea, Chorea gravidarum, Wilson's disease, drug-induced chorea, and metabolic and endocrine-related choreas), a tic (such as motor, phonic, simple, complex, and Tourette syndrome), a dystonia (such as acute, generalized, focal, segmental, sexual, intermediate, psychogenic, and Acute Dystonic Reaction), Sodemytopic Parkinson's, a stereotypic movement disorder (such as movement disorder related to autism, genetic, and childhood), obsessive compulsive disorder, narcolepsy (such as cataplexy), transmissible spongiform encephalopathies (such as Creutzfeldt-Jakob disease and Kuru), neuroacanthocytosis, seizure and convulsions, athetosis (such as related to Huntington's Disease, asphyxia, neonatal jaundice, and stroke), or cerebral palsy.

The present disclosure also provides compounds of Formula Ia-1, Formula Ia-2, Formula Ib-1, Formula Ib-2, Formula Ic-1, Formula Ic-2, Formula Id-1, or Formula Id-2, or pharmaceutically acceptable salt thereof, for treating a dyskinesia (such as levodopa-induced dyskinesia, chronic or tardive dyskinesia, and orofacial dyskinesia), restless leg syndrome (such as drug-induced or idiopathic), a drug-induced dystonia, chorea (such as Huntington's disease, toxin-induced chorea, Sydenham's chorea, Chorea gravidarum, Wilson's disease, drug-induced chorea, and metabolic and endocrine-related choreas), a tic (such as motor, phonic, simple, complex, and Tourette syndrome), a dystonia (such as acute, generalized, focal, segmental, sexual, intermediate, psychogenic, and Acute Dystonic Reaction), Sodemytopic Parkinson's, a stereotypic movement disorder (such as movement disorder related to autism, genetic, and childhood), obsessive compulsive disorder, narcolepsy (such as cataplexy), transmissible spongiform encephalopathies (such as Creutzfeldt-Jakob disease and Kuru), neuroacanthocytosis, seizure and convulsions, athetosis (such as related to Huntington's Disease, asphyxia, neonatal jaundice, and stroke), or cerebral palsy.

The present disclosure also provides compounds of Formula Ia-1, Formula Ia-2, Formula Ib-1, Formula Ib-2, Formula Ic-1, Formula Ic-2, Formula Id-1, or Formula Id-2, or pharmaceutically acceptable salt thereof, in the manufacture of a medicament for treating a dyskinesia (such as levodopa-induced dyskinesia, chronic or tardive dyskinesia, and orofacial dyskinesia), restless leg syndrome (such as drug-induced or idiopathic), a drug-induced dystonia, chorea (such as Huntington's disease, toxin-induced chorea, Sydenham's chorea, Chorea gravidarum, Wilson's disease, drug-induced chorea, and metabolic and endocrine-related choreas), a tic (such as motor, phonic, simple, complex, and Tourette syndrome), a dystonia (such as acute, generalized, focal, segmental, sexual, intermediate, psychogenic, and Acute Dystonic Reaction), Sodemytopic Parkinson's, a stereotypic movement disorder (such as movement disorder related to autism, genetic, and childhood), obsessive compulsive disorder, narcolepsy (such as cataplexy), transmissible spongiform encephalopathies (such as Creutzfeldt-Jakob disease and Kuru), neuroacanthocytosis, seizure and convulsions, athetosis (such as related to Huntington's Disease, asphyxia, neonatal jaundice, and stroke), or cerebral palsy.

The present disclosure also provides compounds of Formula Ia-1, Formula Ia-2, Formula Ib-1, Formula Ib-2, Formula Ic-1, Formula Ic-2, Formula Id-1, or Formula Id-2, or pharmaceutically acceptable salt thereof, or compositions comprising the same, for treating a sleep disorder characterized by disrupted sleep schedule, as well as for treating Parkinson's Disease.

The present disclosure also provides compounds of Formula Ia-1, Formula Ia-2, Formula Ib-1, Formula Ib-2, Formula Ic-1, Formula Ic-2, Formula Id-1, or Formula Id-2, or pharmaceutically acceptable salt thereof, or compositions comprising the same, in the manufacture of a medicament for treating a sleep disorder characterized by disrupted sleep schedule, as well as for treating Parkinson's Disease.

DESCRIPTION OF EMBODIMENTS

Figure 1A:
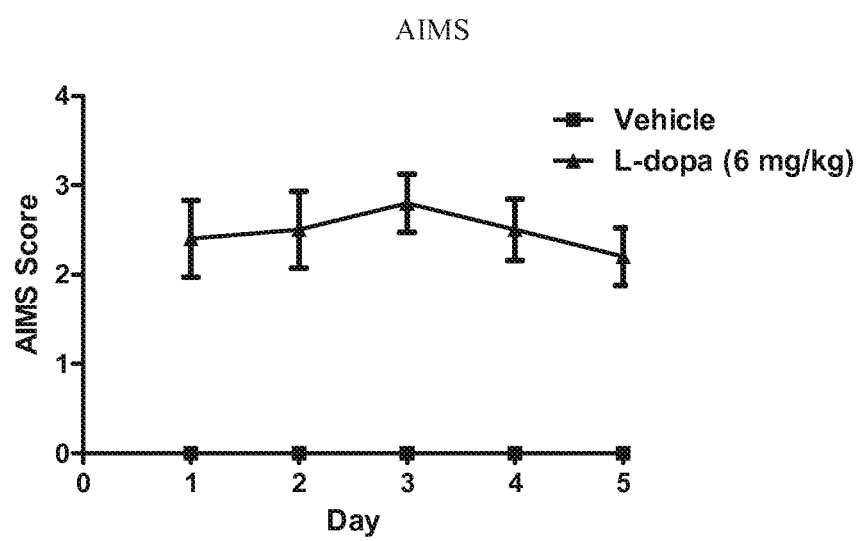
FIGS. 1A and 1B show results of L-dopa administration and Sydnocarb administration, respectively, to 6-OHDA unilaterally lesioned Sprague-Dawley rats.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "alkenyl group" means a monovalent unbranched or branched hydrocarbon chain having one or more double bonds therein. The double bond of an alkenyl group can be unconjugated or conjugated to another unsaturated group. Suitable alkenyl groups include, but are not limited to ($C_2$-$C_6$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

As used herein, the term "alkoxy group" means an —O-alkyl group, wherein alkyl is as defined herein. An alkoxy group can be unsubstituted or substituted with one or two suitable substituents. In some embodiments, the alkyl chain of an alkyloxy group is from 1 to 6 carbon atoms in length, referred to herein, for example, as "($C_1$-$C_6$)alkoxy."

As used herein, the term "alkoxysulfonyl" means the moiety —S(=O)$_2$O-alkyl, wherein alkyl is as defined herein.

As used herein, the term "alkoxysulfonyloxy" means the moiety —OS(=O)$_2$O-alkyl, in which alkyl is as defined herein.

As used herein, the term "alkyl" or "alkyl group" means a saturated, monovalent unbranched or branched hydrocarbon chain. Examples of alkyl groups include, but are not limited to, ($C_1$-$C_6$)alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl group can be unsubstituted or substituted with one or two suitable substituents.

As used herein, the term "alkylsulfonyl" means the moiety —S(=O)$_2$-alkyl, in which alkyl is as defined herein.

As used herein, the term "alkylsulfonylalkyl" means the moiety -alkyl-S(=O)$_2$-alkyl, wherein alkyl (each instance) is as defined herein.

As used herein, the term "alkylsulfonylamino" means the moiety —NHS(=O)$_2$-alkyl, in which alkyl is as defined herein.

As used herein, the term "alkylsulfonyloxy" means the moiety —OS(=O)$_2$-alkyl, wherein alkyl is as defined herein.

As used herein, the term "alkynyl group" means monovalent unbranched or branched hydrocarbon chain having one or more triple bonds therein. The triple bond of an alkynyl group can be unconjugated or conjugated to another unsaturated group. Suitable alkynyl groups include, but are not limited to, (C$_2$-C$_6$)alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein, the term "aminosulfinyl" means the moiety —S(=O)NH$_2$.

As used herein, the term "aminosulfinylalkyl" means the moiety -alkyl-S(=O)NH$_2$, wherein alkyl is as defined herein.

As used herein, the term "aminosulfonyl" means the moiety —S(=O)$_2$NH$_2$.

As used herein, the term "aminosulfonylalkyl" means the moiety -alkyl-S(=O)$_2$—NH$_2$, wherein alkyl is as defined herein.

As used herein, the term "aralkyl" means a moiety having 6 to 20 carbon atoms that combine both an aryl group and an alkyl group, as defined above. Any aralkyl moiety of a compound described herein may optionally be substituted with one or more of the substituent groups mentioned herein.

As used herein, the term "aryl group" means a monocyclic or polycyclic-aromatic radical comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. In some embodiments, the aryl group is a monocyclic ring, wherein the ring comprises 6 carbon atoms, referred to herein as "(C$_6$)aryl."

As used herein, the term "aralkyl" means a moiety having 6 to 20 carbon atoms that combine both an aryl group and an alkyl group, as defined above. Any aralkyl moiety of a compound described herein may optionally be substituted with one or more of the substituent groups mentioned herein.

As used herein, the term "aryloxy group" means an —O-aryl group, wherein aryl is as defined herein. An aryloxy group can be unsubstituted or substituted with one or two suitable substituents. In some embodiments, the aryl ring of an aryloxy group is a monocyclic ring, wherein the ring comprises 6 carbon atoms, referred to herein as "(C$_6$) aryloxy."

As used herein, the term "benzyl" means —CH$_2$-phenyl.

As used herein, the term "carbalkoxy" means the moiety —C(=O)O-alkyl, in which alkyl is as defined herein.

As used herein, the term "carbonyl" group is a divalent group of the formula —C(O)—.

As used herein, the term "carboxamido" means the moiety —C(=O)O—NR'R", in which R' and R", each independently represents H, alkyl, aryl or aralkyl, all as defined herein.

As used herein, the term "compounds described herein" means, collectively, the compounds of Formula I, and pharmaceutically acceptable salts thereof. The compounds are identified herein by their chemical structure and/or chemical name. Where a compound is referred to by both a chemical structure and a chemical name, and that chemical structure and chemical name conflict, the chemical structure is determinative of the compound's identity. The compounds may contain one or more chiral centers and/or double bonds and, therefore, exist as stereoisomers, such as double-bond isomers (i.e., geometric isomers), enantiomers, or diastereomers. The chemical structures depicted herein, and therefore the compounds described herein, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "dialkylaminosulfinyl" means the moiety —S(=O)NR'R" in which R' and R" each, independently, represents H, alkyl, aryl, or aralkyl, all as defined herein.

As used herein, the term "dialkylaminosulfinylalkyl" means the moiety -alkyl-S(=O)NR'R", wherein alkyl is as defined herein, and R' and R" each, independently, represents H, alkyl, aryl or aralkyl, all as defined herein.

As used herein, the term "dialkylaminosulfonyl" means the moiety —S(=O)$_2$NR'R" in which R' and R" each, independently, represents H, alkyl, aryl, or aralkyl, all as defined herein.

As used herein, the term "dialkylaminosulfonylalkyl" means means the moiety -alkyl-S(=O)$_2$—NR'R", wherein alkyl is as defined herein, and R' and R" each, independently, represents H, alkyl, aryl or aralkyl, all as defined herein.

As used herein, the terms "halogen" and "halo" mean fluorine, chlorine, bromine, and/or iodine.

As used herein, the term "heteroaryl group" means a monocyclic- or polycyclic aromatic ring comprising carbon atoms, hydrogen atoms, and one or more heteroatoms, suitably 1 to 3 heteroatoms, independently selected from nitrogen, oxygen, and sulfur. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl (1,2- and 1,4-), pyrimidinyl, tetrazolyl, furyl, thienyl, isoxazolyl, thiazolyl, furyl, phienyl, isoxazolyl, and oxazolyl. A heteroaryl group can be unsubstituted or substituted with one or two suitable substituents. In some embodiments, a heteroaryl group is a monocyclic ring, wherein the ring comprises 2 to 5 carbon atoms and 1 to 3 heteroatoms, referred to herein as "(C$_2$-C$_5$)heteroaryl."

As used herein, the term "heterocycloalkyl group" means a monocyclic or polycyclic ring comprising carbon and hydrogen atoms and at least one heteroatom, suitably, 1 to 3 heteroatoms selected from nitrogen, oxygen, and sulfur, and having no unsaturation. Examples of heterocycloalkyl groups include, but are not limited to, pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. In some embodiments, the heterocycloalkyl group is a monocyclic or bicyclic ring, or a monocyclic ring, wherein the ring comprises from 3 to 6 carbon atoms and form 1 to 3 heteroatoms, referred to herein as $(C_1-C_6)$heterocycloalkyl.

As used herein, the term "heterocyclic radical" or "heterocyclic ring" means a heterocycloalkyl group or a heteroaryl group.

As used herein, the term "hydrocarbyl group" means a monovalent group selected from $(C_1-C_8)$alkyl, $(C_2-C_8)$alkenyl, and $(C_2-C_8)$alkynyl, optionally substituted with one or two suitable substituents. In some embodiments, the hydrocarbon chain of a hydrocarbyl group is from 1 to 6 carbon atoms in length, referred to herein as "$(C_1-C_6)$hydrocarbyl."

As used herein, the term "hydroxysulfonyl" means the moiety —S(=O)$_2$OH.

As used herein, the term "hydroxysulfonyloxy" means the moiety —OS(=O)$_2$OH.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof.

As used herein, the term "isolated" means that the compounds described herein are separated from other components of either (a) a natural source, such as a plant or cell, such as a bacterial culture, or (b) a synthetic organic chemical reaction mixture, such as by conventional techniques.

When administered to a mammal (e.g., to an animal for veterinary use or to a human for clinical use) the compounds described herein may be administered in an isolated form. As used herein, "isolated" means that the compounds are separated from other components of either (a) a natural source, such as a plant or cell, such as bacterial culture, or (b) a synthetic organic chemical reaction mixture, such as, via conventional techniques, the compounds are purified. As used herein, "purified" means that when isolated, the isolate contains at least 90%, or at least 95%, or at least 98%, or at least 99% of a compound by weight of the isolate.

As used herein, the term "monoalkylaminosulfinyl" means the moiety —S(=O)NHR' in which R' is H, alkyl, aryl, or aralkyl, all as defined herein.

As used herein, the term "monoalkylaminosulfinylalkyl" means the moiety -alkyl-S(=O)NHR', wherein alkyl is as defined herein, and R' is H, alkyl, aryl or aralkyl, all as defined herein.

As used herein, the term "monoalkylaminosulfonyl" means the moiety —S(=O)$_2$NHR' in which R' is H, alkyl, aryl, or aralkyl, all as defined herein.

As used herein, the term "monoalkylaminosulfonylalkyl" means means the moiety -alkyl-S(=O)$_2$—NHR', wherein alkyl is as defined herein, and R' is H, alkyl, aryl or aralkyl, all as defined herein.

As used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)" includes, but is not limited to, salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, malonate, mandelate, salicylate, citrate, acid citrate, tartrate, oleate, phthalate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, naphthalenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Examples of organic amines that may serve as salts include, but are not limited to, ammonium, trimethylammonium, diethylammonium, and tris-(hydroxymethyl)methylammonium. Compounds, included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, ammonium, potassium, and iron salts. Another useful salt is L-dopa salt.

As used herein, the term "phenyl" means —C$_6$H$_5$. A phenyl group can be unsubstituted or substituted with one or two suitable substituents.

As used herein, the term "prevention" or "prevent", means a reduction of the risk of acquiring a particular disease or disorder. It need not mean the complete elimination of the disease or disorder.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "purified" means that when isolated, the isolate contains at least 90%, at least 95%, at least 98%, or at least 99% of a compound described herein by weight of the isolate.

As used herein, a "suitable substituent" means a group that does not nullify the synthetic or pharmaceutical utility of the compounds described herein or the intermediates useful for preparing them. Examples of suitable substituents include, but are not limited to: $(C_1-C_8)$alkyl, $(C_1-C_8)$alkenyl, $(C_1-C_8)$alkynyl, $(C_6)$aryl, $(C_3-C_5)$heteroaryl, $(C_3-C_7)$cycloalkyl, $(C_1-C_8)$alkoxy, $(C_6)$aryloxy, —CN, —OH, oxo, halo, —NO$_2$, —CO$_2$H, —NH$_2$, —NH($(C_1-C_8)$alkyl), —N($(C_1-C_8)$alkyl)$_2$, —NH($(C_6)$aryl), —N($(C_6)$aryl)$_2$, —CHO, —CO($(C_1-C_8)$alkyl), —CO($(C_6)$aryl), —CO$_2$($(C_1-C_8)$alkyl), —CO$_2$($(C_6)$aryl), carbalkoxy, carboxamido, alkylsulfonyl, aminosulfinyl, alkylsulfonyloxy, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, and dialkylaminosulfinylalkyl. One of skill in art can readily choose a suitable substituent based on the stability and pharmacological and synthetic activity of the compound described herein.

As used herein, the phrase "therapeutically effective amount" of a composition described herein is measured by the therapeutic effectiveness of a compound described herein, wherein at least one adverse effect of a disorder is ameliorated or alleviated. In one embodiment, the phrase "therapeutically effective amount" of a composition described herein is measured by the therapeutic effectiveness of a compound described herein to treat or prevent dyskinesia. In some embodiments, an effective amount reduces any parameter by which a dyskinesia is measured by at least 10%, by at least 20%, by at least 30%, by at least 40%, by at least 50%, by at least 60%, by at least 70%, by at least 80%, by at least 90%, or by at least 95%.

As used herein, the term "treatment" or "treating" means an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" means inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

At various places in the present specification, substituents of compounds may be disclosed in groups or in ranges. It is specifically intended that the range or group include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

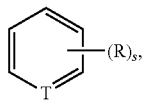

then it is understood that substituent "R" can occur "s" number of times on the ring, and "R" can be a different moiety at each occurrence. Further, in the above example, where the variable T is defined to include hydrogens, such as when T is CH, N, etc., any H can be replaced with a substituent.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

It is understood that the present disclosure encompasses, where applicable, stereoisomers, diastereomers, and optical stereoisomers of the compounds described herein, as well as mixtures thereof, qnd uses thereof. Additionally, it is understood that stereoisomers, diastereomers, and optical stereoisomers of the compounds described herein, and mixtures thereof, are within the scope of the present disclosure. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

To the extent that any of the compounds described herein may be asymmetric (e.g., having one or more stereocenters), all such stereoisomers, such as enantiomers and diastereomers, are intended to be included within the scope of the disclosure unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds are also included within the scope of the disclosure and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallizaion using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

To the extent that the compounds described herein may may include tautomeric forms, all such tautomeric forms are intended to be included. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

A person skilled in the art will recognize that compounds of Formula Ia-1, Formula Ia-2, Formula Ib-1, and Formula Ib-2 are "inner salts" and can exist as depicted. Compounds of Formula 1a are tautomers of the corresponding compounds of Formula 1b. A person skilled in the art will recognize that tautomers may exist as discrete entities in the solid state but that in solution the pairs of tautomers may equilibrate to one or the other tautomeric form or to a mixture of the two tautomers depending on the relative thermodynamic stability of the tautomers in the relevant medium. Compounds depicted in this application encompass the possible tautomeric forms as well as the form (or forms) present upon in vivo administration in the systemic circulation of a mammal.

A person skilled in the art will also recognize that each of these previously mentioned formula's depicts compounds that can be protonated by an external acid resulting in acid addition compounds of Formula Ic-1, Formula Ic-2, Formula Id-1, and Formula Id-2. In each of these compounds, the positive charge in the five membered heterocyclic (e.g., oxadiazole) ring is associated with an anionic negatively charged counter-ion which arises from the external acid. The external acid may be chosen from a list of pharmaceutically acceptable acids such as those described herein.

A person skilled in the art will also recognize that compounds of Formula Ia-1, Formula Ia-2, Formula Ib-1, Formula Ib-2, Formula Ic-1, Formula Ic-2, Formula Id-1, and Formula Id-2 contain a chiral center (when U=C) at the atom position "U" and when the three substituents apart from the heterocyclic ring attached to U are different. The compounds recited in this disclosure encompass both the racemic forms of these chiral compounds as well as the individual enantiomers as depicted in Formula Ia-1, Formula Ia-2, Formula Ib-1, Formula Ib-2, Formula Ic-1, Formula Ic-2, Formula Id-1, or Formula Id-2.

The compounds described herein also include hydrates and solvates, as well as anhydrous and non-solvated forms.

The compounds described herein may also include all isotopes of atoms occurring in the intermediates or final compounds. Isotopes include those atoms having the same atomic number but different mass numbers. For example, isotopes of hydrogen include tritium and deuterium.

In some embodiments, the compounds, or salts thereof, are substantially isolated. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

Although the disclosed compounds are suitable in their stated form, other functional groups can be incorporated into the compound with an expectation of similar results. In particular, thioamides and thioesters are thought to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds described herein may also include derivatives referred to as prodrugs, which can be prepared by modifying functional groups present in the compounds in such a way that the modifications are cleaved, either in routine manipulation or in vivo, to the parent compounds. Examples of prodrugs include compounds of the disclosure as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate, and benzoate derivatives of alcohol and amine functional groups in the compounds of the disclosure. Preparation and use of prodrugs is discussed in T. Higuchi et al., "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference in their entireties.

The compounds described herein can also be altered to contain an amine function, which can form an N-oxide. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

The structures depicted herein may omit necessary hydrogen atoms to complete the appropriate valency. Thus, in some instances a carbon atom or nitrogen atom may appear to have an open valency (i.e., a carbon atom with only two bonds showing would implicitly also be bonded to two hydrogen atoms; in addition, a nitrogen atom with a single bond depicted would implicitly also be bonded to two hydrogen atoms). For example, "—N" would be considered by one skilled in the art to be "—NH$_2$." Thus, in any structure depicted herein wherein a valency is open, a hydrogen atom is implicit, and is only omitted for brevity.

The compounds described herein can also include various charged states. For example, one or more moieties of any of the compounds described herein can be charged. In some instances, any moiety having an amino group can be —NH$_{3+}$. Thus, each amino group existing in any compound described herein can, independently, be either —NH$_2$ or —NH$_3$.

The present disclosure provides one or more compounds of Formula Ia-1, Formula Ia-2, Formula Ib-1, Formula Ib-2, Formula Ic-1, Formula Ic-2, Formula Id-1, or Formula Id-2:

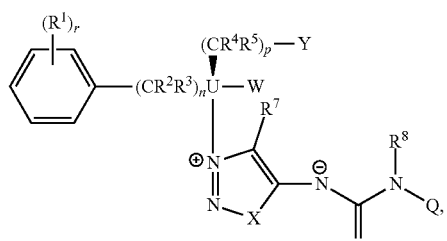
(Ia-1)

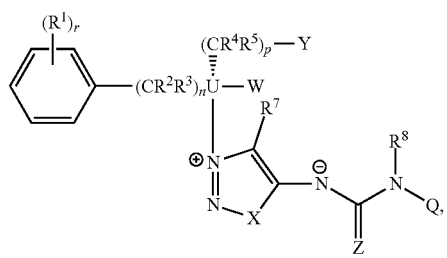
(Ia-2)

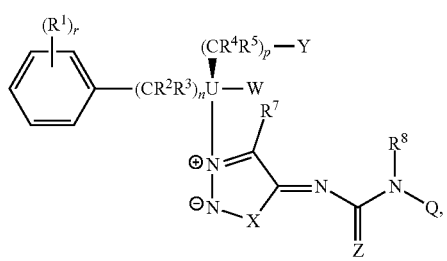
(Ib-1)

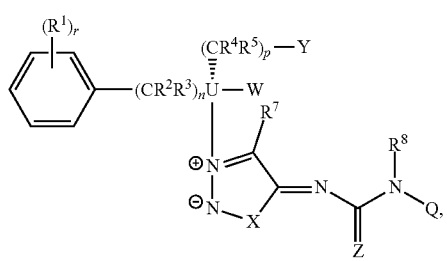
(Ib-2)

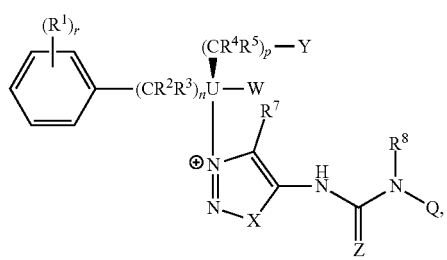
(Ic-1)

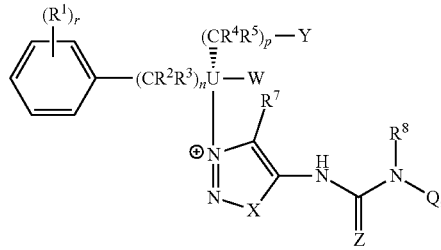
(Ic-2)

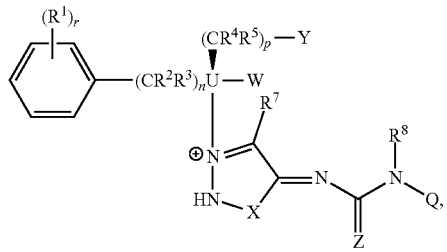
(Id-1)

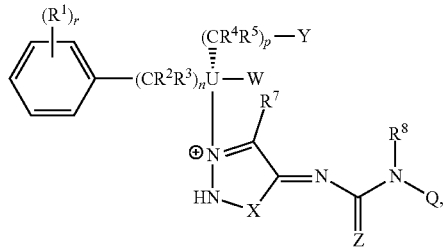
(Id-2)

or a pharmaceutically acceptable salt thereof, wherein: U is C or N; each $R^1$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —N(=O)$_2$, —C(=O)OH, —$NH_2$, —$CF_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl, where r is 0, 1, 2, 3, 4, or 5; each $R^2$ and $R^3$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —C(=O)OH, —$NH_2$, —$CF_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, dialkylaminosulfinylalkyl, aryl, or aryl$C_1$-$C_6$alkyl, where n is 0, 1, 2, 3, or 4; each $R^4$ and R is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —C(=O)OH, —$NH_2$, —$CF_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, dialkylaminosulfinylalkyl, aryl, or aryl$C_1$-$C_6$alkyl, where p is 0, 1, 2, 3, or 4; W is H or $C_1$-$C_6$alkyl; Y is H, $C_1$-$C_6$alkoxy, $C_1$-$C_6$alkylthio, —CN, —OH, —SH, halo, haloalkyl, —NO$_2$, —C(=O)OH, —NH$_2$, —CF$_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or diaalkylaminosulfinylalkyl; X is O or S; Z is O or S; $R^7$ is H or halo; Q is H, $C_1$-$C_6$alkyl, aryl, $C_1$-$C_6$alkylaryl, $C_3$-$C_6$cycloalkyl, or heteroaryl, each of which is optionally substituted with —(R$^6$)$_t$, where t is 0, 1, 2, 3, 4, or 5; $R^8$ is H or $C_1$-$C_6$alkyl; and each $R^6$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —NO$_2$, —N(=O)$_2$, —C(=O)OH, —NH$_2$, —CF$_3$, —O—S(=O)$_2$OH, —NH($C_1$-$C_6$alkyl), —N($C_1$-$C_6$alkyl)$_2$, —C(=O)H, —C(=O)$C_1$-$C_6$alkyl, —C(=O)$C_1$-$C_6$alkoxy, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonly, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl.

In some embodiments, each $R^1$ is, independently, H, $C_1$-$C_6$alkyl, $C_2$-$C_6$alkenyl, $C_1$-$C_6$alkoxy, —CN, —OH, halo, haloalkyl, —NO$_2$, —C(=O)OH, —NH$_2$, —CF$_3$, —NH($C_1$-$C_6$alkyl), —N($C_1$-$C_6$alkyl)$_2$, or —C(=O)H, where r is 1, 2, 3, 4, or 5. In some embodiments, each $R^1$ is, independently, H, $C_1$-$C_6$alkyl, $C_1$-$C_6$alkoxy, —CN, —OH, halo, haloalkyl, —C(=O)OH, —NH$_2$, —CF$_3$, or —C(=O)H, where r is 1, 2, 3, 4, or 5. In some embodiments, each $R^1$ is, independently, H, $C_1$-$C_3$alkyl, $C_1$-$C_3$alkoxy, —CN, —OH, halo, —NH$_2$, or —CF$_3$, where r is 1, 2, 3, 4, or 5. In some embodiments, each $R^1$ is, independently, H, $C_1$-$C_3$alkoxy, —OH, halo, —NH$_2$, or —CF$_3$, where r is 1, 2, 3, 4, or 5. In some embodiments, each $R^1$ is, independently, H, methoxy, ethoxy, F, Cl, Br, —NH$_2$, or —CF$_3$, where r is 1, 2, 3, 4, or 5. In some embodiments, each $R^1$ is, independently, F, Cl, or Br, where r is 1, 2, 3, 4, or 5. In some embodiments, each $R^1$ is F, where r is 1, 2, 3, 4, or 5.

In some embodiments, each $R^2$ and $R^3$ is, independently, H, $C_1$-$C_6$alkyl, $C_2$-$C_6$alkenyl, $C_1$-$C_6$alkoxy, —CN, —OH, halo, haloalkyl, —NO$_2$, —C(=O)OH, —NH$_2$, —CF$_3$, —NH($C_1$-$C_6$alkyl), —N($C_1$-$C_6$alkyl)$_2$, or —C(=O)H, where n is 1, 2, 3, or 4. In some embodiments, each $R^2$ and $R^3$ is, independently, H, $C_1$-$C_3$alkyl, $C_1$-$C_3$alkoxy, —CN, —OH, halo, haloalkyl, —N($C_1$-$C_3$alkyl)$_2$, —NO$_2$, —NH$_2$, or —CF$_3$, where n is 1, 2, 3, or 4. In some embodiments, each $R^2$ and $R^3$ is, independently, H, $C_1$-$C_3$alkyl, —CN, —OH, halo, —N($C_1$-$C_3$alkyl)$_2$, —NH$_2$, or —CF$_3$, where n is 1, 2, 3, or 4. In some embodiments, each $R^2$ and $R^3$ is, independently, H, $C_1$-$C_3$alkyl, —OH, —N($C_1$-$C_3$alkyl)$_2$, or halo, where n is 1, 2, or 3. In some embodiments, each $R^2$ and $R^3$ is, independently, H, F, Cl, or Br, where n is 1 or 2. In some embodiments, each $R^2$ and $R^3$ is, independently, H, F, Cl, or Br, where n is 1. In some embodiments, $R^2$ and $R^3$ are both H and n is 1.

In some embodiments, each $R^4$ and $R^5$ is, independently, H, $C_1$-$C_6$alkyl, $C_2$-$C_6$alkenyl, $C_1$-$C_6$alkoxy, —CN, —OH, halo, haloalkyl, —NO$_2$, —C(=O)OH, —NH$_2$, —CF$_3$, —NH($C_1$-$C_6$alkyl), —N($C_1$-$C_6$alkyl)$_2$, or —C(=O)H, where n is 1, 2, 3, or 4. In some embodiments, each $R^4$ and $R^5$ is, independently, H, $C_1$-$C_3$alkyl, $C_1$-$C_3$alkoxy, —CN, —OH, halo, haloalkyl, —NO$_2$, —NH$_2$, or —CF$_3$, where n is 1, 2, 3, or 4. In some embodiments, each $R^4$ and $R^5$ is, independently, H, $C_1$-$C_3$alkyl, —CN, —OH, halo, —NH$_2$, or —CF$_3$, where n is 1, 2, 3, or 4. In some embodiments, each $R^4$ and $R^5$ is, independently, H, $C_1$-$C_3$alkyl, —CN, or halo, where n is 1, 2, or 3. In some embodiments, each $R^4$ and $R^5$ is, independently, H, F, Cl, or Br, where n is 1 or 2. In some embodiments, each $R^4$ and $R^5$ is, independently, H, F, Cl, or Br, where n is 1. In some embodiments, $R^4$ and $R^5$ are both H and n is 1.

In some embodiments, Y is H, $C_1$-$C_6$alkoxy, —CN, —OH, halo, haloalkyl, —NH$_2$, or —CF$_3$. In some embodiments, Y is H, $C_1$-$C_3$alkoxy, —CN, —OH, or halo. In some embodiments, Y is H, —CN, —OH, F, Cl, or Br. In some embodiments, Y is H, —OH, F, Cl, or Br. In some embodiments, Y is H.

In some embodiments, (CR$^4$R$^5$)$_p$—Y is a $C_1$-$C_6$alkyl. In some embodiments, (CR$^4$R$^5$)$_p$—Y is a $C_1$-$C_3$alkyl. In some embodiments, (CR$^4$R$^5$)$_p$—Y is methyl or ethyl.

In some embodiments, X is O.

In some embodiments, Z is O.

In some embodiments, Q is aryl chosen from anthracenyl, indanyl, indenyl, naphthyl, phenanthrenyl, phenyl, and tetrahydronaphthyl; or heteroaryl chosen from acridinyl, benzimidazolyl, benzofuryl, benzothienyl, benzoxazolyl, benzthiazolyl, carbazolyl, furazanyl, imidazolyl, indazolyl, indolinyl, indolizinyl, indolyl, 3H-indolyl, isobenzofuranyl, isoindolyl, isoquinolyl, isothiazolyl, isoxazolyl, naphthyridinyl, oxadiazolyl, oxazolyl, perimidinyl, phenanthridinyl, phenanthrolinyl, phenazinyl, phenothiazinyl, phenoxazinyl, phthalazinyl, purinyl, pyranyl, pyrazinyl, pyrazolyl, pyridazinyl, pyridyl, pyrimidinyl, pyrrolyl, 2H-pyrrolyl, pyrryl, quinazolinyl, 4H-quinolizinyl, tetrazolyl, 1,2,4-thiadiazolyl, thianthrenyl, thiazolyl, thienyl, triazinyl, triazolyl, and xanthenyl; wherein the aryl or heteroaryl is optionally substituted with —(R$^6$)$_t$, where t is 0, 1, 2, 3, 4, or 5. In some embodiments, Q is aryl chosen from anthracenyl, naphthyl, and phenyl; or heteroaryl chosen from benzimidazolyl, benzofuryl, benzoxazolyl, carbazolyl, furazanyl, imidazolyl, indazolyl, indolinyl, indolizinyl, indolyl, 3H-indolyl, isoindolyl, isoquinolyl, isothiazolyl, isoxazolyl, naphthyridinyl, oxadiazolyl, oxazolyl, purinyl, pyranyl, pyrazinyl, pyrazolyl, pyridazinyl, pyridyl, pyrimidinyl, pyrrolyl, pyrryl, quinazolinyl, thienyl, triazinyl, and triazolyl; wherein the aryl or heteroaryl is optionally substituted with —(R$^6$)$_t$, where t is 0, 1, 2, 3, 4, or 5. In some embodiments, Q is aryl chosen from naphthyl and phenyl; or heteroaryl chosen from benzimidazolyl, benzoxazolyl, imidazolyl, indazolyl, indolinyl, indolyl, isoquinolyl, isoxazolyl, oxazolyl, purinyl, pyranyl, pyrazinyl, pyrazolyl, pyridazinyl, pyridyl, pyrimidinyl, pyrrolyl, pyrryl, thienyl, and triazolyl; wherein the aryl or heteroaryl is optionally substituted with —(R$^6$)$_t$, where t is 0, 1, 2, 3, 4, or 5. In some embodiments, Q is aryl chosen from naphthyl and phenyl; or heteroaryl chosen from benzimidazolyl, imidazolyl, indolyl, oxazolyl, purinyl, pyranyl, pyrazinyl, pyrazolyl, pyridazinyl, pyridyl, pyrimidinyl, pyrrolyl, pyrryl, thienyl, and triazolyl; wherein the aryl or heteroaryl is optionally substituted with —$(R^6)_t$, where t is 0, 1, 2, 3, 4, or 5. In some embodiments, Q is phenyl, pyridazinyl, pyridyl, pyrimidinyl, or triazolyl, each of which is optionally substituted with —$(R^6)_t$, where t is 0, 1, 2, 3, 4, or 5.

In some embodiments, each $R^6$ is, independently, H, —CN, haloalkyl, $C_1$-$C_6$alkyl, $C_1$-$C_6$alkoxy, —OH, halo, —N(=O)$_2$, —C(=O)OH, —NH$_2$, —CF$_3$, —O—S(=O)$_2$OH, —N($C_1$-$C_6$alkyl)$_2$, —C(=O)$C_1$-$C_6$alkyl, or —C(=O)$C_1$-$C_6$alkoxy. In some embodiments, each $R^6$ is, independently, H, $C_1$-$C_3$alkyl, $C_1$-$C_3$alkoxy, —CN, —OH, halo, haloalkyl, —NH$_2$, —CF$_3$, —N(=O)$_2$, —C(=O)OH, —O—S(=O)$_2$OH, —N($C_1$-$C_6$alkyl)$_2$, —C(=O)$C_1$-$C_6$alkyl, or —C(=O)$C_1$-$C_6$alkoxy. In some embodiments, each $R^6$ is, independently, H, $C_1$-$C_3$alkyl, —CN, —OH, halo, —NH$_2$, —CF$_3$, $C_1$-$C_3$alkoxy, —N(=O)$_2$, —C(=O)OH, —O—S(=O)$_2$OH, —N($C_1$-$C_3$alkyl)$_2$, —C(=O)$C_1$-$C_3$alkyl, or —C(=O)$C_1$-$C_3$alkoxy. In some embodiments, each $R^6$ is, independently, H, $C_1$-$C_3$alkyl, $C_1$-$C_3$alkoxy, —OH, halo, —N(=O)$_2$, —C(=O)OH, —NH$_2$, —CF$_3$, —O—S(=O)$_2$OH, —N($C_1$-$C_3$alkyl)$_2$, —C(=O)$C_1$-$C_3$alkyl, or —C(=O)$C_1$-$C_3$alkoxy. In some embodiments, each $R^6$ is, independently, H, F, Cl, or Br. In some embodiments, each $R^6$ is, independently, H or F.

In some embodiments, U is C.
In some embodiments, W is H.
In some embodiments, $R^7$ is H.
In some embodiments, $R^8$ is H.

In some embodiments, each $R^1$ is, independently, H, $C_1$-$C_6$alkyl, $C_2$-$C_6$alkenyl, $C_1$-$C_6$alkoxy, —CN, —OH, halo, haloalkyl, —NO$_2$, —C(=O)OH, —NH$_2$, —CF$_3$, —NH($C_1$-$C_6$alkyl), —N($C_1$-$C_6$alkyl)$_2$, or —C(=O)H, where r is 1, 2, 3, 4, or 5; each $R^2$ and $R^3$ is, independently, H, $C_1$-$C_6$alkyl, $C_2$-$C_6$alkenyl, $C_1$-$C_6$alkoxy, —CN, —OH, halo, haloalkyl, —NO$_2$, —C(=O)OH, —NH$_2$, —CF$_3$, —NH($C_1$-$C_6$alkyl), —N($C_1$-$C_6$alkyl)$_2$, or —C(=O)H, where n is 1, 2, 3, or 4; each $R^4$ and $R^5$ is, independently, H, $C_1$-$C_6$alkyl, $C_2$-$C_6$alkenyl, $C_1$-$C_6$alkoxy, —CN, —OH, halo, haloalkyl, —NO$_2$, —C(=O)OH, —NH$_2$, —CF$_3$, —NH($C_1$-$C_6$alkyl), —N($C_1$-$C_6$alkyl)$_2$, or —C(=O)H, where n is 1, 2, 3, or 4; Y is H, $C_1$-$C_6$alkoxy, —CN, —OH, halo, haloalkyl, —NH$_2$, or —CF$_3$; X is O; Z is O; Q is aryl chosen from anthracenyl, indanyl, indenyl, naphthyl, phenanthrenyl, phenyl, and tetrahydronaphthyl; or heteroaryl chosen from acridinyl, benzimidazolyl, benzofuryl, benzothienyl, benzoxazolyl, benzthiazolyl, carbazolyl, furazanyl, imidazolyl, indazolyl, indolinyl, indolizinyl, indolyl, 3H-indolyl, isobenzofuranyl, isoindolyl, isoquinolyl, isothiazolyl, isoxazolyl, naphthyridinyl, oxadiazolyl, oxazolyl, perimidinyl, phenanthridinyl, phenanthrolinyl, phenazinyl, phenothiazinyl, phenoxazinyl, phthalazinyl, purinyl, pyranyl, pyrazinyl, pyrazolyl, pyridazinyl, pyridyl, pyrimidinyl, pyrrolyl, 2H-pyrrolyl, pyrryl, quinazolinyl, 4H-quinolizinyl, tetrazolyl, 1,2,4-thiadiazolyl, thianthrenyl, thiazolyl, thienyl, triazinyl, triazolyl, and xanthenyl; wherein the aryl or heteroaryl is optionally substituted with —$(R^6)_t$, where t is 0, 1, 2, 3, 4, or 5; each $R^6$ is, independently, H, —CN, haloalkyl, $C_1$-$C_6$alkyl, $C_1$-$C_6$alkoxy, —OH, halo, —N(=O)$_2$, —C(=O)OH, —NH$_2$, —CF$_3$, —O—S(=O)$_2$OH, —N($C_1$-$C_6$alkyl)$_2$, —C(=O)$C_1$-$C_6$alkyl, or —C(=O)$C_1$-$C_6$alkoxy; U is C; W is H; R' is H; and $R^8$ is H.

In some embodiments, each $R^1$ is, independently, H, $C_1$-$C_6$alkyl, $C_1$-$C_6$alkoxy, —CN, —OH, halo, haloalkyl, —C(=O)OH, —NH$_2$, —CF$_3$, or —C(=O)H, where r is 1, 2, 3, 4, or 5; each $R^2$ and $R^3$ is, independently, H, $C_1$-$C_3$alkyl, $C_1$-$C_3$alkoxy, —CN, —OH, halo, haloalkyl, —N($C_1$-$C_3$alkyl)$_2$, —NO$_2$, —NH$_2$, or —CF$_3$, where n is 1, 2, 3, or 4; each $R^4$ and $R^5$ is, independently, H, $C_1$-$C_3$alkyl, $C_1$-$C_3$alkoxy, —CN, —OH, halo, haloalkyl, —NO$_2$, —NH$_2$, or —CF$_3$, where n is 1, 2, 3, or 4; Y is H, $C_1$-$C_3$alkoxy, —CN, —OH, or halo; X is O; Z is O; Q is aryl chosen from anthracenyl, naphthyl, and phenyl; or heteroaryl chosen from benzimidazolyl, benzofuryl, benzoxazolyl, carbazolyl, furazanyl, imidazolyl, indazolyl, indolinyl, indolizinyl, indolyl, 3H-indolyl, isoindolyl, isoquinolyl, isothiazolyl, isoxazolyl, naphthyridinyl, oxadiazolyl, oxazolyl, purinyl, pyranyl, pyrazinyl, pyrazolyl, pyridazinyl, pyridyl, pyrimidinyl, pyrrolyl, pyrryl, quinazolinyl, thienyl, triazolyl, and triazolyl; wherein the aryl or heteroaryl is optionally substituted with —$(R^6)_t$, where t is 0, 1, 2, 3, 4, or 5; each $R^6$ is, independently, H, $C_1$-$C_3$alkyl, $C_1$-$C_3$alkoxy, —CN, —OH, halo, haloalkyl, —NH$_2$, —CF$_3$, —N(=O)$_2$, —C(=O)OH, —O—S(=O)$_2$OH, —N($C_1$-$C_6$alkyl)$_2$, —C(=O)$C_1$-$C_3$alkyl, or —C(=O)$C_1$-$C_3$alkoxy; U is C; W is H; $R^7$ is H; and $R^8$ is H.

In some embodiments, each $R^1$ is, independently, H, $C_1$-$C_3$alkyl, $C_1$-$C_3$alkoxy, —CN, —OH, halo, —NH$_2$, or —CF$_3$, where r is 1, 2, 3, 4, or 5; each $R^2$ and $R^3$ is, independently, H, $C_1$-$C_3$alkyl, —CN, —OH, halo, —N($C_1$-$C_3$alkyl)$_2$, —NH$_2$, or —CF$_3$, where n is 1, 2, 3, or 4; each $R^4$ and $R^5$ is, independently, H, $C_1$-$C_3$alkyl, —CN, —OH, halo, —NH$_2$, or —CF$_3$, where n is 1, 2, 3, or 4; Y is H, $C_1$-$C_3$alkoxy, —CN, —OH, F, Cl, or Br; X is O; Z is O; Q is aryl chosen from naphthyl and phenyl; or heteroaryl chosen from benzimidazolyl, benzoxazolyl, imidazolyl, indazolyl, indolinyl, indolyl, isoquinolyl, isoxazolyl, oxazolyl, purinyl, pyranyl, pyrazinyl, pyrazolyl, pyridazinyl, pyridyl, pyrimidinyl, pyrrolyl, pyrryl, thienyl, and triazolyl; wherein the aryl or heteroaryl is optionally substituted with —$(R^6)_t$, where t is 0, 1, 2, 3, 4, or 5; each $R^6$ is, independently, H, $C_1$-$C_3$alkyl, —CN, —OH, halo, —NH$_2$, —CF$_3$, $C_1$-$C_3$alkoxy, —N(=O)$_2$, —C(=O)OH, —O—S(=O)$_2$OH, —N($C_1$-$C_3$alkyl)$_2$, —C(=O)$C_1$-$C_3$alkyl, or —C(=O)$C_1$-$C_3$alkoxy; U is C; W is H; $R^7$ is H; and $R^8$ is H.

In some embodiments, each $R^1$ is, independently, H, $C_1$-$C_3$alkoxy, —OH, halo, —NH$_2$, or —CF$_3$, where r is 1, 2, 3, 4, or 5; each $R^2$ and $R^3$ is, independently, H, $C_1$-$C_3$alkyl, —OH, —N($C_1$-$C_3$alkyl)$_2$, or halo, where n is 1, 2, or 3; each $R^4$ and $R^5$ is, independently, H, $C_1$-$C_3$alkyl, —CN, or halo, where n is 1, 2, or 3; Y is H, —OH, F, Cl, or Br; X is O; Z is O; Q is aryl chosen from naphthyl and phenyl; or heteroaryl chosen from benzimidazolyl, imidazolyl, indolyl, oxazolyl, purinyl, pyranyl, pyrazinyl, pyrazolyl, pyridazinyl, pyridyl, pyrimidinyl, pyrrolyl, pyrryl, thienyl, and triazolyl; wherein the aryl or heteroaryl is optionally substituted with —$(R^6)_t$, where t is 0, 1, 2, 3, 4, or 5; each $R^6$ is, independently, H, $C_1$-$C_3$alkyl, $C_1$-$C_3$alkoxy, —OH, halo, —N(=O)$_2$, —C(=O)OH, —NH$_2$, —CF$_3$, —O—S(=O)$_2$OH, —N($C_1$-$C_3$alkyl)$_2$, —C(=O)$C_1$-$C_3$alkyl, or —C(=O)$C_1$-$C_3$alkoxy; U is C; W is H; $R^7$ is H; and $R^8$ is H.

In some embodiments, each $R^1$ is, independently, H, methoxy, ethoxy, F, Cl, Br, —NH$_2$, or —CF$_3$, where r is 1, 2, 3, 4, or 5; each $R^2$ and $R^3$ is, independently, H, F, Cl, or Br, where n is 1 or 2; each $R^4$ and $R^5$ is, independently, H, F, Cl, or Br, where n is 1 or 2; Y is H; X is O; Z is O; Q is phenyl, pyridazinyl, pyridyl, pyrimidinyl, or triazolyl, each of which is optionally substituted with —$(R^6)_t$, where t is 0, 1, 2, 3, 4, or 5; each $R^6$ is, independently, H, F, Cl, or Br; U is C; W is H; $R^7$ is H; and $R^8$ is H.

In some embodiments, each $R^1$ is, independently, F, Cl, or Br, where r is 1, 2, 3, 4, or 5; each $R^2$ and $R^3$ is, independently, H, F, Cl, or Br, where n is 1; each $R^4$ and $R^5$ is, independently, H, F, Cl, or Br, where n is 1; Y is H; X is O; Z is O; Q is phenyl, pyridazinyl, pyridyl, pyrimidinyl, or triazolyl, each of which is optionally substituted with —$(R^6)_t$, where t is 0, 1, 2, 3, 4, or 5; each $R^6$ is, independently, H or F; U is C; W is H; $R^7$ is H; and $R^8$ is H.

In some embodiments, each $R^1$ is F, where r is 1, 2, 3, 4, or 5; $R^2$ and $R^3$ are both H and n is 1; $R^4$ and $R^5$ are both H and n is 1; Y is H; X is O; Z is O; Q is phenyl, pyridazinyl, pyridyl, pyrimidinyl, or triazolyl, each of which is optionally substituted with —$(R^6)_t$, where t is 0, 1, 2, 3, 4, or 5; each $R^6$ is, independently, H or F; U is C; W is H; $R^7$ is H; and $R^8$ is H.

Illustrative examples of compounds that are encompassed by Formula I and that may be useful in the methods described herein include, but are not limited to, sydnocarb (U is C; r is 0; $R^2$ and $R^3$ are both H; n is 1; $R^4$ and $R^5$ are both H; p is 1; W is H; Y is H; X is O; Z is O; $R^7$ is H; Q is phenyl; t is 0; and $R^8$ is H), hydroxysydnocarb (U is C; r is 0; $R^2$ and $R^3$ are both H; n is 1; $R^4$ and $R^5$ are both H; p is 1; W is H; Y is H; X is O; Z is O; $R^7$ is H; Q is phenyl; t is 1; $R^6$ is —OH— in para position; and $R^8$ is H), or dihydroxysydnocarb (U is C; r is 0; one of $R^2$ and $R^3$ is H and the other of $R^2$ and $R^3$ is —OH; n is 1; $R^4$ and R are both H; p is 1; W is H; Y is H; X is H; Z is; R is H; Q is phenyl; t is 1; $R^6$ is —OH in para position; and $R^8$ is H).

In some embodiments, the compound(s), or pharmaceutically acceptable salt thereof, is chosen from any one or more of the following (including any enantiomer thereof):

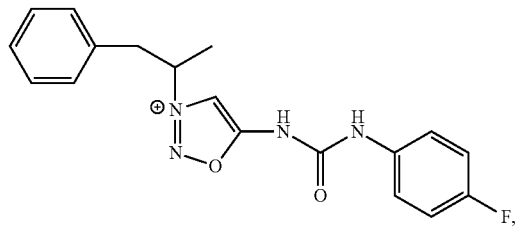

,

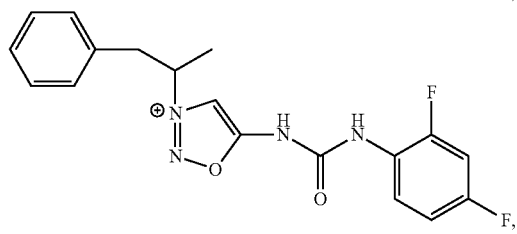

,

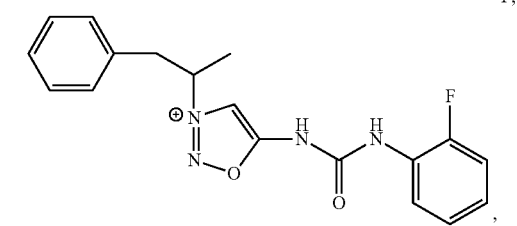

,

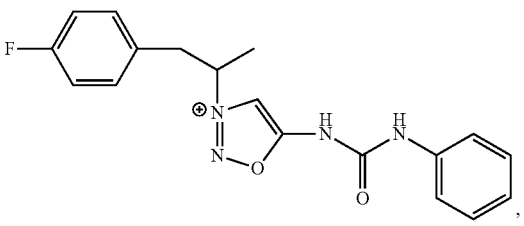

,

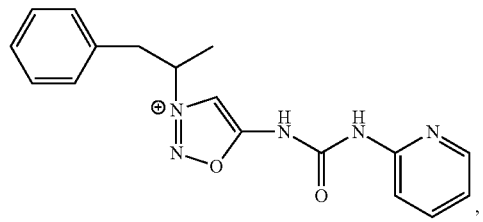

,

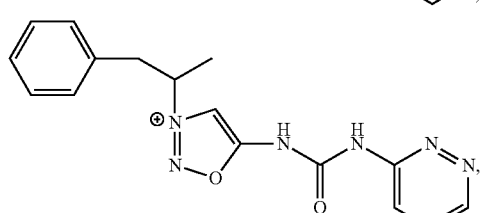

,

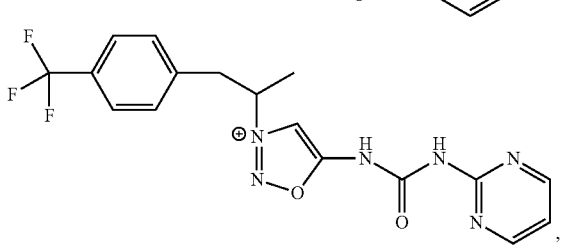

,

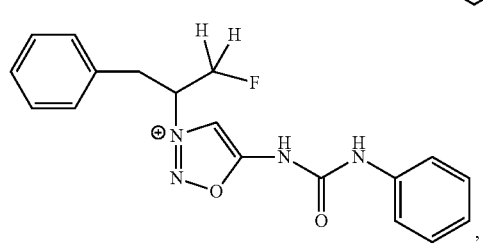

,

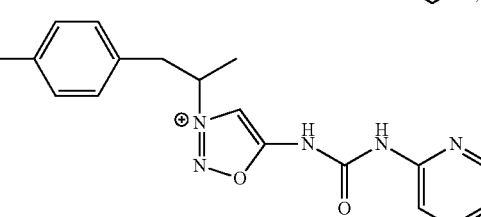

,

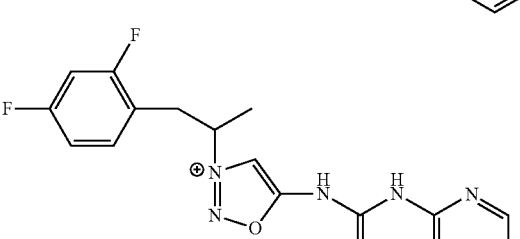

,

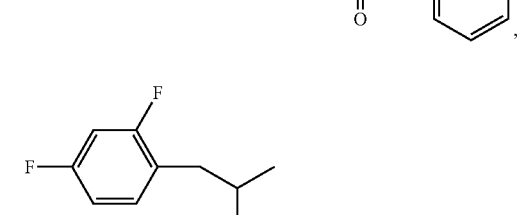

, and

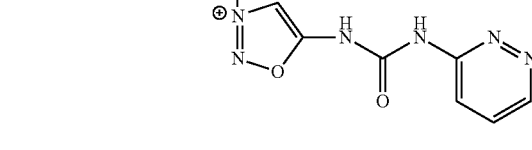

.

In some embodiments, the compound(s), or pharmaceutically acceptable salt thereof, is chosen from any one or more of the following (including any enantiomer thereof):

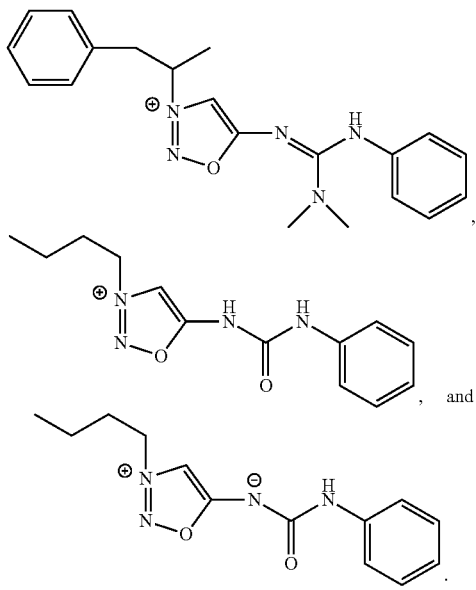

In some embodiments, the compound is not sydnocarb; hydroxysydnocarb; dihydroxysydnocarb; N-phenylcarbamoyl-3-(benzyl)-sydnonimine; N-(3',4'-dichlorophenyl)carbamoyl-3-phenethyl-sydnonimine; N-(p-chlorophenyl)carbamoyl-3-phenethylsydnonimine; N-(m-trifluoromethyl) carbamoyl-3-phenethylsydnonimine; 3-(benzyl) sydnonimine-N-phenylcarbamoyl; 3-(p-methyl-benzyl) sydnonimine-N-phenylcarbamoyl; 3-(phenylpropyl) sydnonimine-N-phenylcarbamoyl; 3-(p carboxylbenzyl) sydnonimine-N-phenylcarbamoyl; 3-(p-fluorobenzy-1) sydnonimine-N-phenylcarbamoyl; 3-phenethylsydnonimine-N-(3'-4'-dichloro-phenyl)carbamoyl; and 3-(p-nitrophenethyl)-sydnonimine-N-(3',4'-dinitrophenyl)carbamoyl; or a pharmaceutically acceptable salt thereof.

It will be understood that the compounds described herein are illustrative only and not intended to limit the scope of the claims to only those compounds.

The compounds described herein can be prepared by organic chemistry techniques known to those of ordinary skill in the art. For example the compounds described herein can be prepared as described in, for example, GB Patent No. 1,262,830, U.S. Patent Application Publication No. 2008/0319030, and U.S. Patent Application Publication No. 2011/0288137, which are incorporated herein by reference in its entirety.

Preparation of the compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety. Suitable hydroxyl protecting groups include, but are not limited to, tert-butyldimethylsilyl (TBS), methoxymethyl ether (MOM), tetrahydropyranyl ether (THP), t-Butyl ether, allyl ether, benzyl ether, t-Butyldimethylsilyl ether (TBDMS), t-Butyldiphenylsilyl ether (TBDPS), acetic acid ester, and the like.

The compounds described herein also include derivatives referred to as prodrugs, which can be prepared by modifying functional groups present in the compounds in such a manner that the modifications are cleaved, either in routine manipulation or in vivo, to the parent compounds. Prodrugs are intended to include any covalently bonded carriers that release an active parent drug of described herein in vivo when such prodrug is administered to a mammalian subject. Examples of prodrugs include compounds as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi et al., "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

The present disclosure also provides compositions comprising one or more of the compounds of Formula I. In some embodiments, the composition is a pharmaceutical composition that comprises a pharmaceutically acceptable carrier.

In some embodiments, the compositions may comprise a therapeutically effective amount of a compound described herein, optionally more than one compound described herein, optionally in purified form, together with a suitable amount of a pharmaceutically acceptable carrier.

Carriers include diluents, adjuvants, excipients, or other vehicles with which a compound described herein is administered. Such pharmaceutical carriers can be liquids, such as water and oils, including those of petroleum, animal, vegetable or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a patient, the compounds described herein and pharmaceutically acceptable carriers are suitably sterile. Water is a suitable carrier when the compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carriers is a capsule (see e.g., U.S. Pat. No. 5,698,155). Other examples of suitable pharmaceutical carriers are described in Remington's Pharmaceutical Sciences, A. R. Gennaro (Editor) Mack Publishing Co.

In some embodiments, the compounds described herein are formulated in accordance with routine procedures as a pharmaceutical composition adapted for intravenous administration to human beings. Typically, compounds described herein for intravenous administration are solutions in sterile isotonic aqueous buffer. Where necessary, the compositions may also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the compound described herein is to be administered by infusion, it can be dispensed, for example, with an infusion bottle containing sterile pharmaceutical grade water or saline. Where the compound described herein is administered by injection, an ampoule of sterile water for injection or saline can be provided so that the ingredients may be mixed prior to administration.

The compositions described herein can also be prepared for oral administration. Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds described herein. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate may also be used. Oral compositions can include standard carriers such as mannitol, lactose, starch, magnesium stearate, sodium saccharine, cellulose, magnesium carbonate, etc. Such carriers are suitably of pharmaceutical grade.

The amount of a compound described herein that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound described herein per kilogram body weight. In some embodiments, the oral dose is 0.01 milligram to 70 milligrams per kilogram body weight, or 0.1 milligram to 50 milligrams per kilogram body weight, or 0.5 milligram to 20 milligrams per kilogram body weight, or 1 milligram to 10 milligrams per kilogram body weight. In some embodiments, the oral dose is 5 milligrams of a compound described herein per kilogram body weight. The dosage amounts described herein refer to total amounts administered; that is, if more than one compound described herein is administered, the dosages correspond to the total amount of the compounds described herein administered. Oral compositions can contain 10% to 95% active ingredient by weight.

Suitable dosage ranges for intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound described herein per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds described herein for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

The present disclosure also provides pharmaceutical packs or kits comprising one or more containers filled with one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration. In some embodiments, the kit contains more than one compound described herein. In some embodiments, the kit comprises a compound described herein and another therapeutic agent, such as any of those described herein.

The compounds described herein can be assayed in vitro and in vivo, for the desired therapeutic or prophylactic activity, prior to use in humans. For example, in vitro assays can be used to determine whether administration of a specific compound described herein or a combination of compounds described herein is suitable for treating dyskinesia. The compounds described herein may also be demonstrated to be effective and safe using animal model systems.

Other methods will be known to the skilled artisan and are within the scope of the disclosure.

In some embodiments, the compounds described herein can be used and/or formulated in combination therapy with at least one other therapeutic agent (i.e., one or more other therapeutic agents). The compound described herein and the additional therapeutic agent can act additively or synergistically. In some embodiments, a composition comprising a compound described herein is administered concurrently with the administration of another therapeutic agent, which can be part of the same composition as the compound described herein or a different composition. In another embodiment, a composition comprising a compound described herein is administered prior or subsequent to administration of another therapeutic agent. In some embodiments, combination therapy involves alternating between administering a composition comprising a compound described herein and a composition comprising another therapeutic agent, e.g., to minimize the toxicity associated with a particular drug. The duration of administration of each drug or therapeutic agent can be, e.g., one month, three months, six months, or a year. In certain embodiments, when a composition described herein is administered concurrently with another therapeutic agent that potentially produces adverse side effects including, but not limited to, toxicity, the therapeutic agent can advantageously be administered at a dose that falls below the threshold at which the adverse side is elicited.

In some embodiments, the additional therapeutic agent is: 1) an anti-Parkinsonian agent; 2) an agent used to treat dyskinesias; and/or 3) an agent that induces other types of dyskinesias. One or more of these agents can be combined with a compound described herein either in the same composition, formulation, or dosage form, or combined into a single administration (e.g. concurrent administration) to a mammal. These agents can be used in the amount already indicated for a mammal or in a dose that is less than the acceptable dose.

In some embodiments, the anti-Parkinsonian agent is: 1) an agent used for dopamine replacement including, but not limited to, L-dopa and L-dopa/carbidopa (SINEMET®); 2) a dopamine uptake blocker including, but not limited to, modafinil (PROVIGIL®), benocyclidine, and amfonelic acid; 3) a dopamine agonist including, but not limited to, apomorphine (Apokyn, Ixense, Spontane, and Uprima), bromocriptine (Parlodel and Cycloset), cabergoline (Dostinex and Cabaser), lisuride (Dopergin, Proclacam, and Revanil), pergolide (Permax), ropinirole (Requip, Ropark, and Adartrel), pramipexole (Mirapex, Mirapexin, and Sifrol), and rotigotine (Neupro); 4) an anti-cholinergic including, but not limited to, trihyexyphenidyl (Artane, Apo-Trihex, Parkin, and Pacitane) and benzatropine (Cogentin); 5) an MAO inhibitor including, but not limited to, selegiline (Anipryl, L-deprenyl, Eldepryl, Emsam, and Zelapar) and ginko biloba; and 6) a COMT inhibitor including, but not limited to, tolcapone (Tasmar) and entacapone (Comtan).

In some embodiments, the agent used to treat dyskinesias is: 1) a glutamate receptor antagonist including, but not limited to, amantadine (Symmetrel), dextrorphan, dextromorphan, MK-801 (Dizocilpine), and Co-101,244/PD-174, 494; 2) an AMPA receptor, including, but not limited to, retigabine (Trobalt, Potiga), flupirtine (Katadolon, Trancolong, Awegal, Efiret, Trancopal Dolo, and Metanor), topirimate (Topamax), GYK-47,261, and IEM-1460; 3) a mGluR5 including, but not limited to, MRZ-8676, AFQ056 (Mavoglurant), ADX-48,621, 2-Methyl-6-(phenylethynyl)pyridine (MPEP), and 3-((2-Methyl-4-thiazolyl)ethynyl)pyridine (MTEP); 4) a Glutamate release inhibitor including, but not limited to, riluzole (RILUTEK®) and naftazone; 5) an opioid including, but not limited to, U50-488, morphine (Avinza, Kadian, Oramorph, Roxanol, and Kapanol), meperidine (DEMEROL®), and methadone (Symoron, Dolophine, Amidone, Methadose, Physeptone, Heptadon); 6) a Serotonergic including, but not limited to, buspirone (Buspar), clozapine (Clozaril), quetiapine (Seroquel, Xeroquel, and Ketipinor), MDMA (3,4-methylenedioxy-N-methamphetamine) (Ecstasy), pimavenserin, ritanserin, citalopram (Celexa, Cipramil), and fluoxetine (Prozac, Sarafem, Fontex); 7) a GABA compound including, but not limited to, diazepam (Diastat, Valium) and zolpidem (Ambien, Ambien CR, Intermezzo, Stilnox, and Sublinox); 8) an Adenosine compound including, but not limited to, istradefylline and preladenant; 9) a Cannabinioid including, but not limited to, rimonabant (Acomplia, Bethin, Monaslim, Remonabent, Riobant, Slimona, Rimoslim, Zimulti, and Riomont) and nabilone (Cesamet); 10) an Adrenergic including, but not limited to, Idazoxan, Yohimbine (Yocon), Rauwolscine (isoyohimbine, α-yohimbine, and corynanthidine), Fipamezole, and propanolol (Inderal, Inderal LA, Avlocardyl, Deralin, Dociton, Inderalici, InnoPran XL, Sumial, Anaprilinum, Bedranol SR); 11) a histamine including, but not limited to, famotidine (Pepcid), immepip, and Imetit; 12) a Cholinergic including, but not limited to, nicotine, rivastigmine (Exelon), and donepezil (Aricept); and 13) another agent including, but not limited to, tamoxifen (Nolvadex, Istubal, Valodex), sildenafil (Viagra), and Uk-343,664.

In some embodiments, the agent that induces other types of dyskinesias is an Antipsychotic including, but not limited to, chlorpromazine (Thorazine, Largactil, Megaphen), metoclopramide (Reglan), promethazine (Phenergan, Promethegan, Romergan, Fargan, Farganesse, Prothiazine, Avomine, Atosil, Receptozine, Lergigan, and Sominex), olanzapine (Zyprexa), risperidone (Risperdal), clozapine (Clozaril), aripiprazole (Abilify, Aripiprex).

In some embodiments, the additional agent is not an anti-epileptic agent. Anti-epileptic agent(s) are chosen from carbamazepine, lamotrigine, phenobarbital, phenyloin, topiramate, valproate and zonisamide. In some embodiments, the anti-convulsant or anti-epileptic agent(s) is chosen from carbamazepine, gabapentin, lamotrigine, levetiracetam, oxcarbazepine, phenyloin, pregabalin, rufinamide, valproate and topiramate. In some embodiments, the anti-convulsant or anti-epileptic agent(s) is chosen from gabapentin, lamotrigine, levetiracetam, pregabalin, rufinamide, valproate and topiramate. Examples of anti-convulsant or anti-epileptic agents include, but are not limited to, the following, described non-exclusively by either mode of action or chemical class: a) AMPA antagonists such as AMP-397, E-2007, NS-1209, talampanel, perampanel, and the like; b) benzodiazepines such as diazepam, lorazepam, clonazepam, clobazam, clorazepate, midazolam, nimetazepam, nitrazepam, temasepam, and the like; c) barbiturates such as phenobarbital, amobarbital, methylphenobarbital, primidone, barbexaclone sodium, metharbital, pentobarbital, and the like; d) valproates (including fatty acid derivatives) such as valproic acid, valproate semisodium, valpromide, divalproex, valnoctamide, and the like; e) GABA related agents such as gabapentin (2-[1-(aminomethyl)cyclohexyl]acetic acid), pregabalin ((S)-3-(aminomethyl)-5-methylhexanoic acid), vigabatrin, and the like; f) AEDs such as losigamone, retigabine, rufinamide (1-[(2,6-difluorophenyl)methy-1]triazole-4-carboxamide), SPD-421 (DP-VPA), T-2000, XP-13512, and the like; g) iminostilbenes such as carbamazepine, oxcarbazepine, and the like; h) hydantoins such as phenyloin sodium, phenyloin, mephenyloin, fosphenyloin sodium, ethotoin, and the like; h) NMDA antagonists such as harkoseride, and the like; i) sodium channel blockers such as BIA-2093, CO-102862, lamotrigine, and the like; j) succinimides such as methsuximide, ethosuximide, phensuximide, mesuximide, and the like; k) carboxylic acids such as tiagabine, and the like; l) AEDS such as acetazolamide, clomthiazole, edisilate, zonisamide, felbamate, topiramate, tiagabine, levetiracetam, briveracetam, GSK-362115, GSK-406725, ICA-69673, CBD *cannabis* derivative, isovaleramide (NPS-177 6), RWJ-333369 (carisbamate), safinamide, seletracetam, soretolide, stiripentol, valrocemide, and the like; inm) oxazolidinediones such as trimethadione, paramethadione, ethadione and the like; n) pyrrolidines such as levetiracetam, and the like; o) sulphonamides, such as acetazolamide, methazolamide, zonisamide, sultiame, and the like; p) aminobutyric acids and the like; q) sulfamate-substituted monosaccharides such as topiramate (2,3:4,5-Bis-0-(1-methylethylidene)-beta-D-fructopyranose sulfamate)), and the like; r) carboxamides such as carbamazepine, oxcarbazepine, rufinamide, and the like; s) aromatic allylic alcohols such as stiripentol, and the like; t) ureas such as phenacemide, pheneturide, and the like; u) phenyltriazines such as lamotrigine, and the like; v) carbamates such as emylcamate, felbamate, meprobamate, and the like; w) pyrrolidines such as brivaracetam, levetriacetame, nefiracetam, selectracetam, and the like; and x) Eugenols such as (4-allyl-2-methoxyphenol), phenyleugenol, benzyleugenol, and phenylethyl eugenol.

The present disclosure also provides methods of treating a dyskinesia or another disorder in a mammal comprising administering to the mammal in need thereof an effective amount of a compound of Formula Ia-1, Formula Ia-2, Formula Ib-1, Formula Ib-2, Formula Ic-1, Formula Ic-2, Formula Id-1, or Formula Id-2:

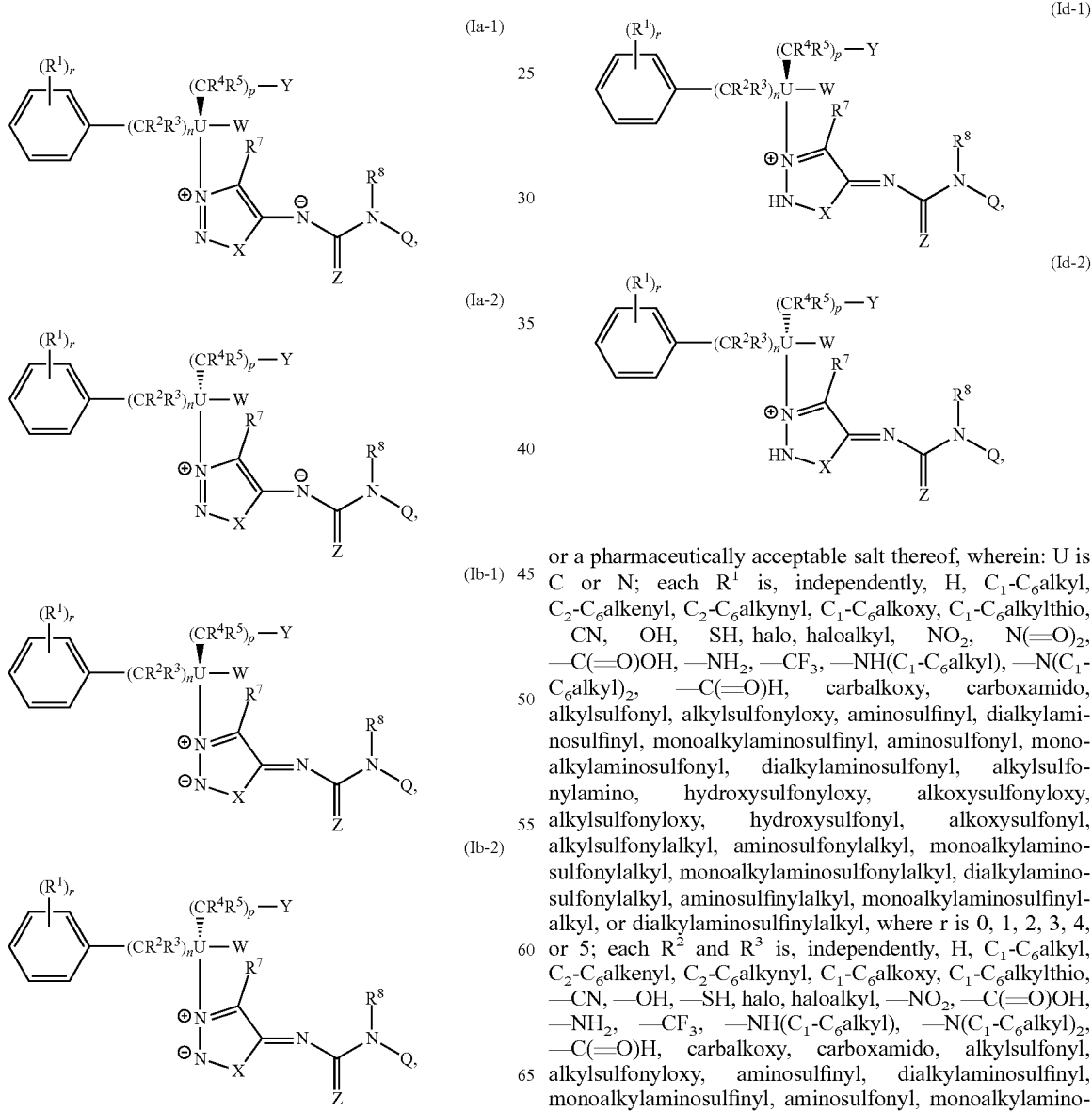

or a pharmaceutically acceptable salt thereof, wherein: U is C or N; each $R^1$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —N(=O)$_2$, —C(=O)OH, —$NH_2$, —$CF_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, monoalkylaminosulfonylalkyl, dialkylaminosulfonylalkyl, aminosulfinylalkyl, monoalkylaminosulfinylalkyl, or dialkylaminosulfinylalkyl, where r is 0, 1, 2, 3, 4, or 5; each $R^2$ and $R^3$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —C(=O)OH, —$NH_2$, —$CF_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, dialkylaminosulfinylalkyl, aryl, or aryl$C_1$-$C_6$alkyl, where n is 0, 1, 2, 3, or 4; each $R^4$ and $R^5$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —C(=O)OH, —$NH_2$, —$CF_3$. —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonyl alkyl, dialkyl aminosulfonyl alkyl, aminosulfinylalkyl, monoalkylaminosulfinylalkyl, dialkylaminosulfinylalkyl, aryl, or aryl$C_1$-$C_6$alkyl, where p is 0, 1, 2, 3, or 4; W is H or $C_1$-$C_6$alkyl; Y is H, $C_1$-$C_6$alkoxy, $C_1$-$C_6$alkylthio, —CN, —OH, —SH, halo, haloalkyl, —$NO_2$, —C(=O)OH, —$NH_2$, —$CF_3$, —NH($C_1$-$C_6$alkyl), —N($C_1$-$C_6$alkyl)$_2$, —C(=O)H, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl; X is O or S; Z is O or S; $R^7$ is H or halo; Q is H, $C_1$-$C_6$alkyl, aryl, $C_1$-$C_6$alkylaryl, $C_3$-$C_6$cycloalkyl, or heteroaryl, each of which is optionally substituted with —($R^6$)$_t$, where t is 0, 1, 2, 3, 4, or 5; $R^8$ is H or $C_1$-$C_6$alkyl; and each $R^6$ is, independently, H, $C_1$-$C_6$alkyl, $C_2$-$C_6$alkenyl, $C_2$-$C_6$alkynyl, $C_1$-$C_6$alkoxy, $C_1$-$C_6$alkylthio, —CN, —OH, —SH, halo, haloalkyl, —$NO_2$, —N(=O)$_2$, —C(=O)OH, —$NH_2$, —$CF_3$, —O—S(=O)$_2$OH, —NH($C_1$-$C_6$alkyl), —N($C_1$-$C_6$alkyl)$_2$, —C(=O)H, —C(=O)$C_1$-$C_6$alkyl, —C(=O)$C_1$-$C_6$alkoxy, carbalkoxy, carboxamido, alkylsulfonyl, alkylsulfonyloxy, aminosulfinyl, dialkylaminosulfinyl, monoalkylaminosulfinyl, aminosulfonyl, monoalkylaminosulfonyl, dialkylaminosulfonyl, alkylsulfonylamino, hydroxysulfonyloxy, alkoxysulfonyloxy, alkylsulfonyloxy, hydroxysulfonyl, alkoxysulfonyl, alkylsulfonylalkyl, aminosulfonylalkyl, monoalkylaminosulfonylalkyl, dialkylaminosulfonylalkyl, aminosulfinylalkyl, monoalkylaminosulfinylalkyl, or dialkylaminosulfinylalkyl; or pharmaceutically acceptable salt thereof, wherein the another disorder is restless leg syndrome (such as drug-induced or idiopathic), a drug-induced dystonia, chorea (such as Huntington's disease, toxin-induced chorea, Sydenham's chorea, Chorea gravidarum, Wilson's disease, drug-induced chorea, and metabolic and endocrine-related choreas), a tic (such as motor, phonic, simple, complex, and Tourette syndrome), a dystonia (such as acute, generalized, focal, segmental, sexual, intermediate, psychogenic, and Acute Dystonic Reaction), Sodemytopic Parkinson's, a stereotypic movement disorder (such as movement disorder related to autism, genetic, and childhood), obsessive compulsive disorder, narcolepsy (such as cataplexy), transmissible spongiform encephalopathies (such as Creutzfeldt-Jakob disease and Kuru), neuroacanthocytosis, seizure and convulsions, athetosis (such as related to Huntington's Disease, asphyxia, neonatal jaundice, and stroke), or cerebral palsy.

The present disclosure also provides methods of treating and/or preventing dyskinesia.

In some embodiments, a composition described herein comprising a compound described herein and a pharmaceutically acceptable carreier is administered to a mammal, such as a human, with dyskinesia and/or disorders associated with dyskinesia.

The disclosure provides methods of treatment and prophylaxis by administration to a patient of a therapeutically effective amount of a composition comprising a compound described herein. The patient is a mammal, including, but not limited, to a cow, horse, sheep, pig, chicken, turkey, quail, cat, dog, mouse, rat, rabbit, guinea pig, etc., and is more suitably a human.

The present compositions, which comprise one or more compounds described herein, can be administered orally. The compounds described herein may also be administered by any other convenient route, for example, by infusion or bolus injection, by absorption through epithelial or mucocutaneous linings (e.g., oral mucosa, rectal and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer a compound described herein. In some embodiments, more than one compound described herein is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner, and will depend in-part upon the site of the medical condition. In most instances, administration will result in the release of the compounds described herein into the bloodstream. In some embodiments, the frequency of dosing is once per day (qd).

In some embodiments, it may be desirable to administer one or more compounds described herein locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

Pulmonary administration can also be employed, e.g., by use of an inhaler or nebulizer, and formulation with an aerosolizing agent, or via perfuision in a fluorocarbon or synthetic pulmonary surfactant. In certain embodiments, the compounds described herein can be formulated as a suppository, with traditional binders and vehicles such as triglycerides.

In another embodiment, the compounds described herein can be delivered in a vesicle, in particular a liposome (see Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In some embodiments, the compounds described herein can be delivered in a controlled release system. In some embodiments, a pump may be used (see Langer, supra; Sefton, 1987, *CRC Crit. Ref Biomed. Eng.* 14:201; Buchwald et al., 1980, *Surgery* 88:507 Saudek et al., 1989, *N.*

*Engl. J. Med.* 321:574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In some embodiments, a controlled-release system can be placed in proximity of the target of the compounds described herein, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, *Science* 249:1527-1533) may be used.

In some embodiments, the compounds, compositions, formulations, and/or dosage forms can be used to treat and/or prevent a dyskinesia. In some embodiments, the dyskinesia is levodopa-induced dyskinesia (LID). LID can be present in patients with Parkinson's disease who have been on levodopa for prolonged periods of time. Three forms of dyskinesia have been classified on the basis of their course and presentation following an oral dose of L-dopa: i) off-period dystonia (correlated to the akinesia that occurs before the full effect of L-dopa sets in, when the plasma levels of L-dopa are low); ii) diphasic dyskinesia (occurs when plasma levodopa levels are rising or falling; this form is usually dystonic or ballistic; does not respond to L-dopa reduction); and iii) peak-dose dyskinesia (the most common form of LID; it correlates with stable L-dopa plasma level). In some embodiments, the dyskinesia is chronic or tardive dyskinesia. Tardive dyskinesia occurs after treatment with an antipsychotic drug such as haloperidol or amoxapine. Tardive dyskinesia often involves involuntary lip smacking, repetitive pouting of the lips, and tongue protrusions. In some embodiments, the dyskinesia is orofacial dyskinesia (e.g., Rabbit syndrome), which may be related to persistent replication of Herpes Simplex Virus type-1.

In some embodiments, the compounds, compositions, formulations, and/or dosage forms can be used to treat and/or prevent other disorders. In some embodiments, the disorder is restless leg syndrome (e.g., drug-induced or idiopathic). In some embodiments, the disorder is a drug-induced dystonia. In some embodiments, the disorder is a chorea (e.g., Huntington's disease; toxin-induced chorea; Sydenham's chorea; Chorea gravidarum; Wilson's disease; drug-induced chorea; and metabolic and endocrine-related choreas). In some embodiments, the disorder is a tic (e.g., motor; phonic; simple; complex; and Tourette syndrome). In some embodiments, the disorder is a dystonia (e.g., acute; generalized; focal; segmental; sexual; intermediate; psychogenic; and Acute Dystonic Reaction). In some embodiments, the disorder is Sodemytopic Parkinson's. In some embodiments, the disorder is a stereotypic movement disorder (e.g., related to autism; genetic; and childhood). In some embodiments, the disorder is obsessive compulsive disorder. In some embodiments, the disorder is narcolepsy (e.g., cataplexy). In some embodiments, the disorder is transmissible spongiform encephalopathies (e.g., Creutzfeldt-Jakob disease; and Kuru). In some embodiments, the disorder is neuroacanthocytosis. In some embodiments, the disorder is seizure and convulsions. In some embodiments, the disorder is athetosis (e.g., related to Huntington's Disease; asphyxia; neonatal jaundice; and stroke). In some embodiments, the disorder is cerebral palsy.

In some embodiments, the compounds and/or compositions described herein are not used for treatment of: epilepsy; Parkinson's disease; pulmonary conditions such as lung edema; ischemia-reperfusion injury; cardiac conditions, such as acute decompensated heart failure and the cardiorenal syndrome; hyperprolactinaemia (BrE), hyperprolactinemia (AmE) and microprolactinoma; pain including chronic or neuropathic pain; catatonic, dyskinesia, restless legs syndrome and related movement disorders; stress, chronic posttraumatic stress disorder, anxiety disorders, obsessive-compulsive disorders, postpartum depression; schizophrenia, manic, bipolar, and affective disorder; executive function disorders, such as ADHD, Tourette syndrome and autism; cocaine, amphetamine, alcohol dependency, and addictive behavior, such as pathological gambling; neuroendocrinal regulatory disorders; inflammatory conditions, autoimmune diseases and rheumatism; neoplastic disorders, such as pituitary carcinomas, macroprolactinomas; visual sensory disorders, color deficiency; and ejaculatory and related sexual dysfunction.

In some embodiments, the compounds disclosed herein are not used in combination with L-dopa for the treatment of Parkinson's disease; or in combination with a selective serotonin reuptake inhibitor (SSRI) for the treatment of depression and/or cocaine abuse and addiction; or in combination with dopamine D2 antagonist for the treatment of schizophrenia; or in combination with cholinergic modulators for the treatment of Alzheimer disease or other diseases or conditions in which patients have a cognitive deficit; or in combination with an anti-epileptic agent for the treatment of Tardive dyskinesia.

There are notable side effects of L-dopa treatment that are not associated with dyskinesia including, but not limited to, hypotension; arrhythmias; nausea; gastrointestinal bleeding; disturbed respiration; hair loss; disorientation and/or confusion; extreme emotional states, particularly anxiety, but also excessive libido; vivid dreams and/or insomnia; auditory and/or visual hallucinations; effects on learning; somnolence and narcolepsy; and stimulant psychosis. In some embodiments, treatment with a compound or composition described herein decreases or eliminates one or more of these side effects.

In addition, serious side-effects in the treatment of Parkinson's disease are the effects of chronic levodopa administration, including but not limited to: end-of-dose deterioration of function; on off oscillations; freezing during movement; dose failure (drug resistance); dyskinesia at peak dose (levodopa-induced dyskinesia); possible serotonin depletion; and possible dopamine dysregulation. In some embodiments, treatment with a compound or composition described herein decreases or eliminates one or more of these side effects.

The present disclosure provides methods for treating Parkinson's Disease comprising administering to a human in need thereof an effective amount of a compound of Formula Ia-1, Formula Ia-2, Formula Ib-1, Formula Ib-2, Formula Ic-1, Formula Ic-2, Formula Id-1, or Formula Id-2, as described herein. In some embodiments, the compound of Formula Ia-1, Formula Ia-2, Formula Ib-1, Formula Ib-2, Formula Ic-1, Formula Ic-2, Formula Id-1, or Formula Id-2 being administered is present within any of the compositions disclosed herein. In some embodiments, the human administered any one or more of the compounds of Formula I is also administered L-dopa. In some embodiments, the L-dopa and the compound of Formula I is present within the same composition or dosage form.

The present disclosure provides methods for treating a sleep disorder characterized by disrupted sleep schedule comprising administering to a human in need thereof an effective amount of a compound of Formula Ia-1, Formula Ia-2, Formula Ib-1, Formula Ib-2, Formula Ic-1, Formula Ic-2, Formula Id-1, or Formula Id-2, as described herein. In some embodiments, the compound of Formula Ia-1, Formula Ia-2, Formula Ib-1, Formula Ib-2, Formula Ic-1, Formula Ic-2, Formula Id-1, or Formula Id-2 being administered is present within any of the compositions disclosed herein. Not desiring to be bound by any particular theory, the compounds of Formula I may act by restoring normal sleep architecture and/or normal circadian rhythm. Examples of sleep disorders associated with altered sleep rhythm and/or architecture include, but are not limited to, insomnia, restless legs syndrome, narcolepsy, and REM sleep behavior disorder; disorders associated with neurodegenerative diseases such as Alzheimer's disease, Parkinson's disease, and multiple sclerosis; disrupted REM sleep disorder associated with drug withdrawal, especially alcohol or sedative-hypnotic withdrawal; and disrupted circadian rhythm associated with sleep apnia, shift work and jet lag.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

U.S. Provisional Ser. No. 61/786,714 filed Mar. 15, 2013 is incorporated herein by reference in its entirety.

EXAMPLES

Example 1: Rat Model for Parkinsons' Disease

The neurotoxin 6-hydroxydopamine (6-OHDA) is widely used to induce depletion of dopaminergic neurons in animal models of Parkinson's disease (PD). Unilateral administration of 6-OHDA into the median forebrain bundle can produce a 90-95% ipsilateral depletion of dopamine neurons in 80-90% of animals injected, leading to a PD-like motor dysfunction. Treatment of lesioned animals with L-dopa can have varying effects on motor performance in this model. The current study evaluated sydnocarb in a 6-OHDA lesioned, L-dopa treated rat model of PD.

Female, Sprague-Dawley rats (Charles River Laboratories) at 7 to 8 weeks of age were used. Animals were assigned randomly to treatment groups. The diet consisted of standard rodent chow and water ad libitum.

6-OHDA was formulated at 5 mg/ml solution in 0.03% ascorbic acid in sterile 0.9% NaCl. Three μL of 6-OHDA was injected into the median forebrain bundle at the following stereotaxic coordinates from bregma: Anteroposterior (A/P) −4.0 mm; mediolateral (M/L) −1.3 mm; ventrodorsal (V/D) −8.0 mm with reference to the top of the skull.

After lesion, rats were allowed to recover for two weeks and then tested for amphetamine-induced rotational activity. Animals were treated with 25 mg/kg amphetamine in saline and recorded in an open-field chamber for 90 minutes. Only rats rotating greater than 4 times per minute were used in efficacy studies. After an additional one week, rats were treated with L-dopa (Isotec IY0630) at various times and measured for the appearance of abnormal involuntary movements (AIMs).

The AIMs test was carried out as follows: 1) weigh rat and inject with L-dopa/benserazide (10 ml/kg, ip); may be a single injection per day over multiple days; administration of a test compound or reference compound may also be included; 2) place rat in empty cage, start video recording; 3) AIMs were assessed in four areas: a) onset of symptoms-latency (seconds) to first visual AIM as defined below; b) 30 minute AIM score; c) 60 minute AIM score; and d) number of left rotations from 30-60 minutes; 4) AIMs were scored and recorded on a scale from 0 to 4: i) absent; ii) slight left forelimb dystonia with grooming; iii) excessive left forelimb dystonia with grooming; iv) left forelimb dystonia with left circling; and v) continuous left circling with or without grooming; 5) record any unusual clinical signs; and 6) after 60 minutes, stop recording, place rat back into home cage.

Figure 1B:
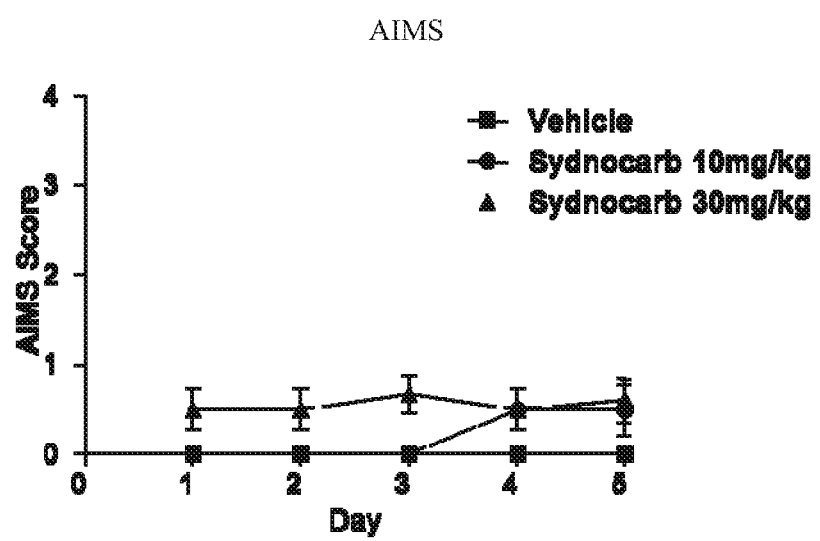

As shown in FIG. 1A, L-dopa (6 mg/kg) was administered once daily for 5 days to 6-OHDA unilaterally lesioned Sprague-Dawley rats that had previously been selected based on rotational response to amphetamine treatment (N=10-11l/group). Sixty minutes after injection, abnormal involuntary movements (AIMs) were scored. Treatment with L-dopa produced significantly higher AIMs scores compared to vehicle-treated rats. As shown in FIG. 1B, treatment of once daily Sydnocarb (10 and 30 mg/kg) did not cause significant AIMs compared to vehicle-treated rats. As shown in FIGS. 1A and 1B, L-dopa causes significant AIMs compared to the vehicle group, where as Sydnocarb alone does not cause significant AIMs. These data demonstrate the establishment of a validated preclinical model of Parkinson's disease.

Example 2: Reduction of L-Dopa-Induced Dyskinesia

Figure 2:
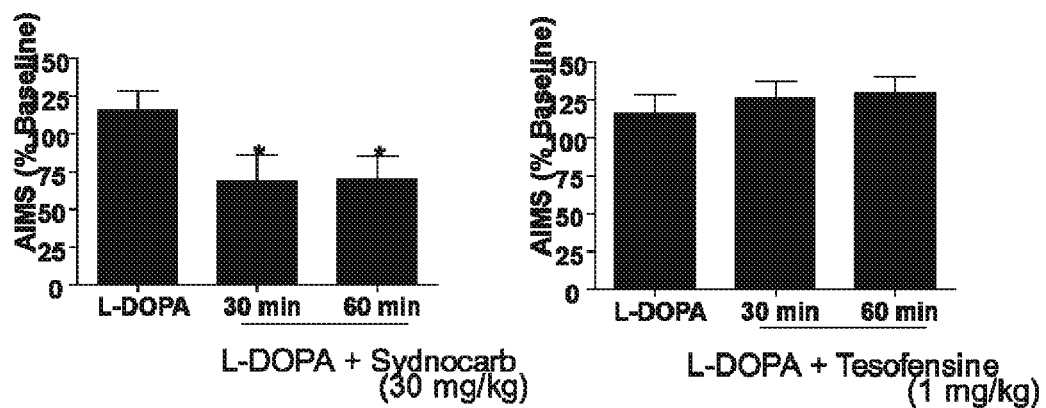
FIG. 2 shows that Sydnocarb, but not Tesofensine, ameliorates L-dopa-induced dyskinesia in 6-OHDA-treated rats.

Rats receiving a unilateral 6-OHDA lesion as described above were treated with L-dopa (day 1, 50 mg/kg) and then L-dopa and test drug (day 2, Sydnocarb or Tesofensine). A two-day treatment with L-dopa caused an increase in abnormal involuntary movements (AIMs) that was ameliorated with Sydnocarb but not Tesofensine treatment. Results are shown in FIG. 2. As shown in FIG. 2, Sydnocarb, but not Tesofensine, ameliorates L-dopa-induced dyskinesia in 6-OHDA-treated rats.

Treatment with L-dopa caused an increase in ATMs that was reduced approximately 40% by Sydnocarb administered 30 min after L-dopa administration. This effect was seen 30 and 60 minutes after L-dopa administration. Tesofensine, a non-specific catecholamine reuptake inhibitor administered under the same conditions, had no affect on AIMs in this study. These data show that Sydnocarb can reduce L-dopa-induced dyskinesias in a preclinical model of PD, and that it is functionally differentiated from non-specific DAT inhibitors such as Tesofensine.

Example 3: Enhancement of L-Dopa-Mediated Anti-Akinesia

In 6-OHDA-lesioned rats, L-dopa administration also elicits a therapeutically beneficial anti-akinetic activity that can be measured by the forelimb adjusting step (FAS) test. To determine the effect of Sydnocarb on L-dopa efficacy on this motor function, 6-OHDA-lesioned rats were treated with L-dopa in combination with Sydnocarb at 10 mg/kg and assessed by the FAS test (see, FIG. 3). Treatment with L-dopa for two days resulted in an increase in motor function compared to vehicle controls. Administration of 10 mg/kg Sydnocarb with L-dopa resulted in significantly higher adjusting step scores compared to vehicle controls, as well as increased scores compared to L-dopa alone.

The Forelimb Adjusting Step Test was carried out as follows:

Handling & Training:

For three consecutive days, the experimenter that performed the study handled the rats so they were familiar with the experimenter's grip: the rat was held with one hand fixing the hindlimbs and slightly raising the hind part above the surface; the other hand fixed the forelimb not to be monitored; the forelimb to be monitored was touching the table; the animal was moved slowly sideways (approx. 5 sec for 90 cm), first in the forehand and then in the backhand; and these steps were repeated for the other forelimb. Forehand is defined as compensating movement toward the body and backhand is defined as compensating movement away from the body.

Testing:

Each stepping test consisted of six trials for each forepaw, alternating between directions both forehand and backhand as follows: the rat was held in the same position as described above with one paw touching the table; the rat was moved slowly sideways (approx 5 sec for 90 cm), first in the forehand and then in the backhand; the number of adjusting steps for both paws in the forehand and back hand directions of movement were counted and recorded; and the sequence of testing was left paw forehand and backhand adjusting stepping, followed by right paw backhand and forehand directions. The rat was returned to its home cage and the sequence repeated with the second rat in the cage. Five more trials were performed for each rat, placing the rats back in their home cage between trials.

Dosing:

This portion of the experiment was run 3-4 weeks post 6-OHDA lesion, and at least 1 week post rotations testing as follows: prior to the start of dosing, rats were trained and baselines performed as above; preparation of L-dopa with benserazide (concentrations are for i.p. injection, 10 ml/kg): a) L-dopa dissolved in saline at 1.2 mg/ml; and b) benserazide dissolved in saline at 0.4 mg/ml; preparation of sydnocarb 10 mg/kg (concentrations are for i.p. injection, 10 ml/kg): a) sydnocarb dissolved in 0.5% methylcellulose, 0.2% tween 80 in dH$_2$O at 1 mg/ml.

Day 1

Rats were weighed and injected with L-dopa/benserazide (12 mg/kg/4 mg/kg). FAS were run approximately 60 minutes post L-dopa/benserazide dose. Rats were returned to home cage.

Day 2

Rats were weighed and injected with sydnocarb 10 mg/kg or vehicle (0.5% methylcellulose, 0.2% tween 80 in dH$_2$O), 30 minutes prior to L-dopa/benserazide dosing. The rest of the study was continued as described in Day 1.

Data were represented as percent by summing steps (forward and backhand) of the lesioned forelimb and dividing by the sum of the steps of the intact forelimb and multiplying by 100, giving a measure of the degree of forepaw disability. A similar calculation was obtained for percent of lesioned forelimb, giving a measure of gain of function.

Figure 3:
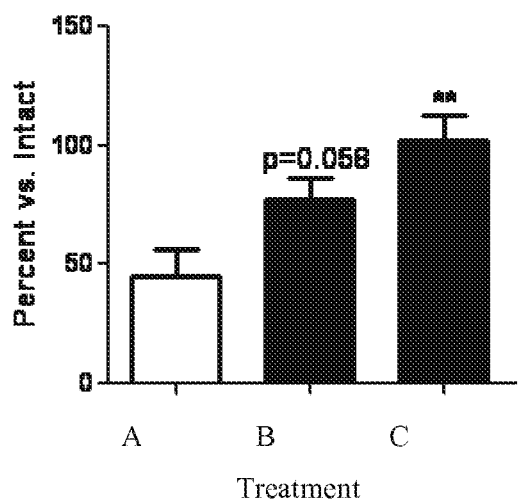
FIG. 3 shows the effect of Sydnocarb on L-dopa efficacy on motor function.

As shown in FIG. 3, assessment of L-dopa induced motor effects in 6-OHDA treated rats was examined. Sprague-Dawley rats (6/group) were injected unilaterally with 6-OHDA as described above. Two weeks later, rats were tested for amphetamine-induced rotation activity to verify the dopaminergic lesion. After an additional one week, rats were treated with L-dopa at 12 mg/kg (day 1) and then L-dopa and sydnocarb at 10 mg/kg (day 2). Forepaw adjusting steps were scored and graphed as a percent of the intact (unaffected) forelimb. Treatment with L-dopa produced a slight increase in steps compared to vehicle (untreated). Sydnocarb at 10 mg/kg produced a significant increase (virtually back to 100%) in adjusting steps compared to vehicle. (**$p<0.01$, $p=0.058$, One-way ANOVA with post-hoc t-test compared to veh+veh). These results establish a rat model of L-dopa-induced step testing and show that Sydnocarb can enhance the motor performance effects of L-dopa. Moreover, Sydnocarb may allow the use of lower therapeutic doses of L-dopa, thereby reducing potential L-dopa-induced side effects.

Example 4: Mouse Open Field Activity

Figure 4:
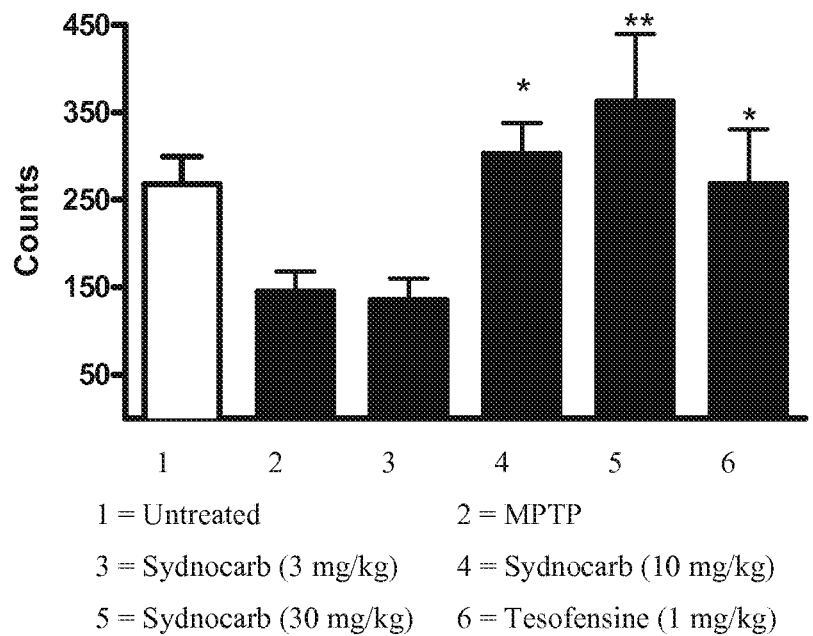
FIG. 4 shows results of an Open Field Activity assay in which locomotor and sensorimotor parameters were evaluated.

An Open Field Activity assay was performed in which locomotor and sensorimotor parameters were evaluated in an automated open-field apparatus. 1-methyl-4-phenyl-1,2,3,6-tetrahydropyridine (MPTP) injections (3×20 mg/kg) were performed in C57Bl/6 mice at two-hour intervals (final dose of MPTP=60 mg/kg). Mice were treated with the compound 30 minutes prior to MPTP and daily for 4 days. Locomotor activity was monitored on day 5, thirty minutes after administration of test compound. Locomotor activity was measured in an automated open-field (MedAssociates) for 30 minutes. The following parameters were measured: 1) horizontal distance traveled, 2) number of rearing events and 3) stereotypic behavior. Results for vertical activity (rearing events) are shown in FIG. 4.

Both Sydnocarb and Tesofensine prevent decrease in vertical activity in C57Bl/6 mice treated with MPTP. These data indicate that Sydnocarb can prevent uptake of toxic MPTP, consistent with the mechanism of DAT inhibition, and can prevent symptomatic movement disorders in a preclinical model of PD.

Example 5: Mouse Electroencephalogram

Electroencephalographic data were obtained in C57Bl/6 mice chronically implanted with electrodes to monitor brain and muscular activity. The percent time spent awake was evaluated following intraperitoneal injections of Sydnocarb 4 hours after lights-on, when mice are predominantly sleeping. Results are shown in FIG. 5.

Figure 5:
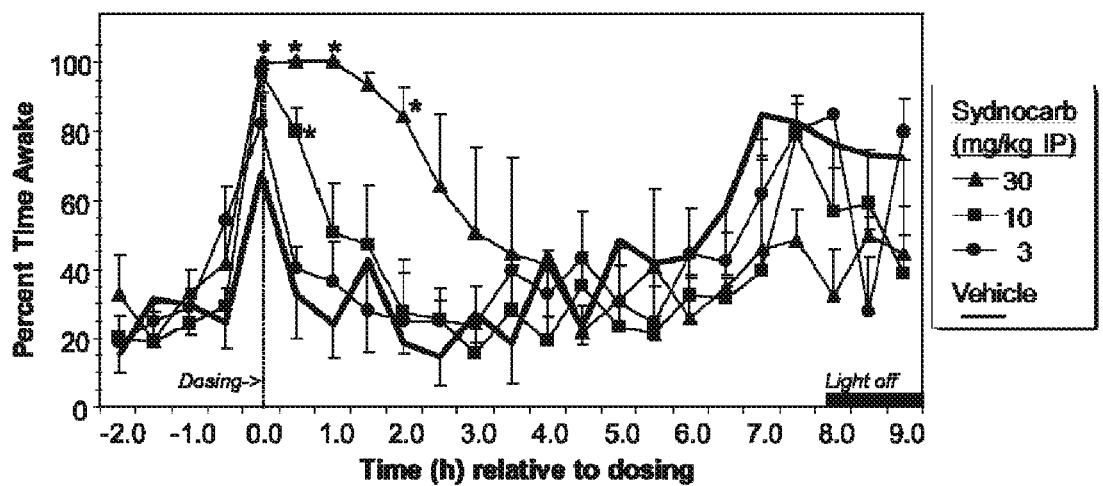
FIG. 5 shows Sydnocarb dose-dependently increased time awake compared to vehicle controls upon electroencephalographic analysis to monitor brain and muscular activity.

As shown in FIG. 5, Sydnocarb dose-dependently increased time awake compared to vehicle controls. These data indicate that Sydnocarb may alleviate sleep disruption and disorders that are associated with PD.

Example 6: Reduction of L-Dopa-Induced Dyskinesia: Chronic Dosing

The effects of Sydnocarb on abnormal involuntary movements (AIMs) in unilaterally lesioned 6-OHDA rats that were treated with L-dopa with and without Sydnocarb for 2 weeks was examined.

Drug Treatment

L-dopa was administered at a dose level of 12 mg/kg (ip) along with benserazide (ip; 4 mg/kg). Sydnocarb (10 or 30 mg/kg, ip), amantadine (40 mg/kg ip), or vehicle was administered 30 minutes prior to L-dopa/benserazide. As a "priming" step, L-dopa was administered daily by itself for 1 week after the amphetamine rotation wash-out period.

Subsequently, Sydnocarb, along with L-dopa, was dosed daily for an additional 12 days.

Abnormal in Voluntary Movements (AIMs)

The effects of chronic L-dopa, alone or in combination with Sydnocarb, were evaluated by rating individual animals for abnormal limb, oral and facial movements based on methods described in Cenci et al., Nat. Rev. Neurosci., 2002, 3,574-9. After treatment, rats were placed in a confined chamber and monitored for axial, limb, and orolingual AIMs every 20-30 minutes for 2 hours as follows:
1. For the first minute, AIMs were assessed in three areas:
   a. Axial: dystonic posturing of the neck and torso in a twisted manner directed toward the side of the body contralateral to the lesion;
   b. Forelimb: rapid, purposeless movements of the forelimb located on the side of the body contralateral to the lesion; and
   c. Orolingual: repetitive openings and closings of the jaw and tongue protrusions occurring at times when the rats are not chewing or knowing on food or other objects.
2. AIMs were scored and recorded on a scale from 0 to 4:
   0=not present;
   1=present for less than 50% of the observation period;
   2=present for 50% or more of the observation period;
   3=present for the entire observation period but interrupted by a loud stimulus (a tap on the cage); and
   4=present for the entire observation period and not interrupted by a loud stimulus.
3. For the second minute, contralateral rotations, defined as complete 360° turns away from the lesioned side of the brain, were tallied.
4. Ipsilateral rotations were counted as negative numbers and thus, deducted from the total contralateral rotations.
5. For each AIMs subcategory, the scores were summed for the entire testing period.

Assessment of L-Dopa Induced Dyskinesia in 6-OHDA Treated Rats

Figure 6:
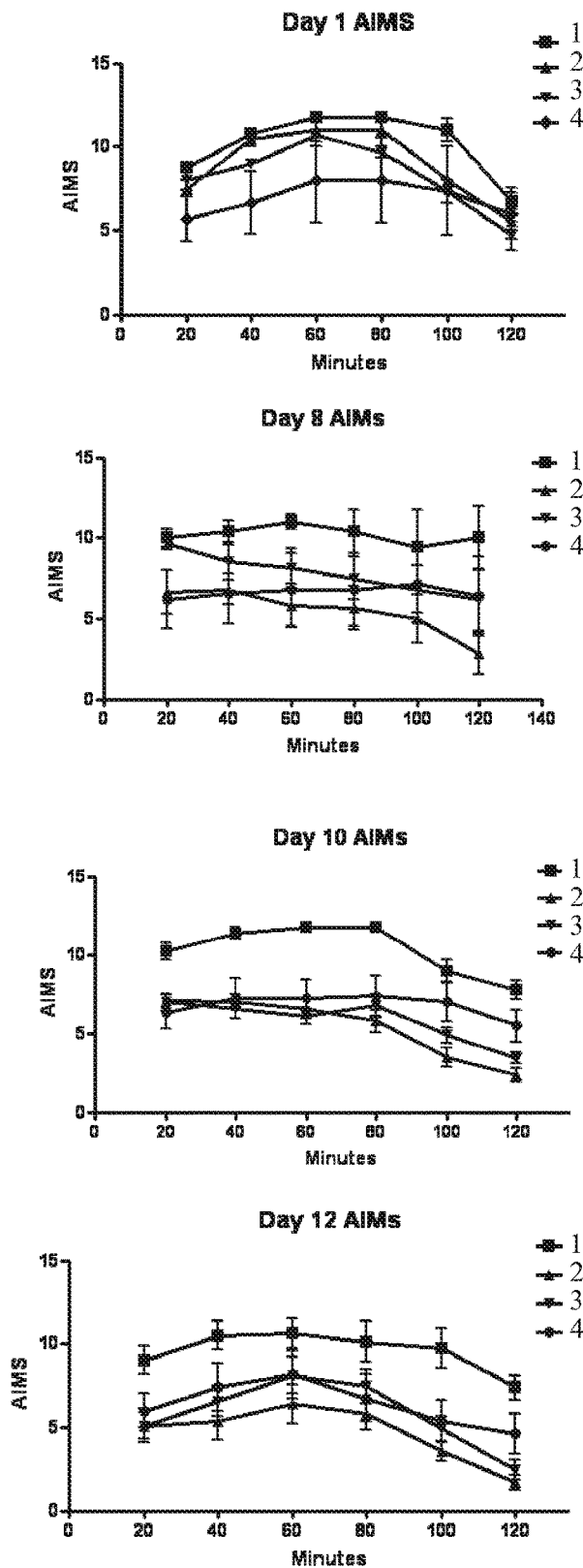
FIG. 6 shows the effects of chronic L-dopa, alone or in combination with Sydnocarb, evaluated by rating individual animals for abnormal limb, oral and facial movements.

Sprague-Dawley rats (10/group) were injected unilaterally with 6-OHDA as described previously. Two weeks later, rats were tested for amphetamine-induced rotation activity to verify the dopaminergic lesion. After an additional one week, baseline AIMs were measured and rats were treated with L-dopa at 12 mg/kg and Sydnocarb at 10 and 30 mg/kg (ip) for 12 days. On days 1, 8, 10, and 12, AIMs were scored every 20 minutes for 2 hours and graphed as a sum of axial, limb, and orolingual (ALO) abnormal movements (FIG. 6). Treatment with this dose of L-dopa produced an increase in AIMS compared to baseline. Treatment with Sydnocarb produced a decrease in AIMs compared to vehicle.

Example 7: Reduction of L-Dopa-Induced Dyskinesia: Oral Dosing

Assessment of Sydnocarb Plasma Drug Levels in Sprague-Dawley Rats (3/Group)

Figure 7:
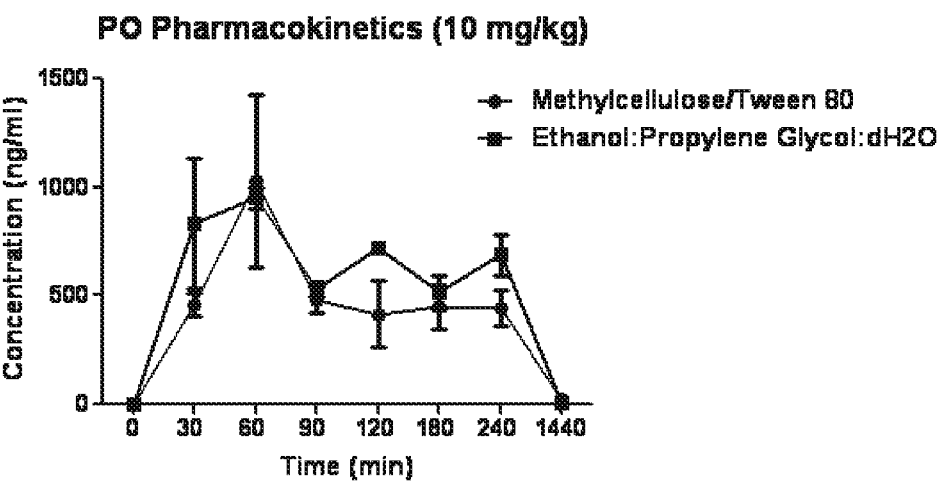
FIG. 7 shows PK profiles of drug formulations demonstrating the ethanol-based formulation produces slightly higher plasma levels at several time points.

Rats were administered Sydnocarb via oral gavage (po) at 10 mg/kg and plasma isolated at various times post-dose. Sydnocarb was formulated in two different vehicles (0.5% methylcellulose/0.2% Tween-80, and Ethanol:Propylene glycol:water (1:3:1)). Comparison of these two drug vehicles was performed in a pharmacokinetic (PK) study to determine if an ethanol-based formulation, which produced better solubility, had similar properties as the standard methylcellulose formulation used in previous studies. Plasma samples were analyzed for drug levels by standard LC/MS techniques and reported as ng/ml. Both drug formulations produced similar PK profiles, with the ethanol-based formulation producing slightly higher plasma levels at several time points (FIG. 7).

Figure 8:
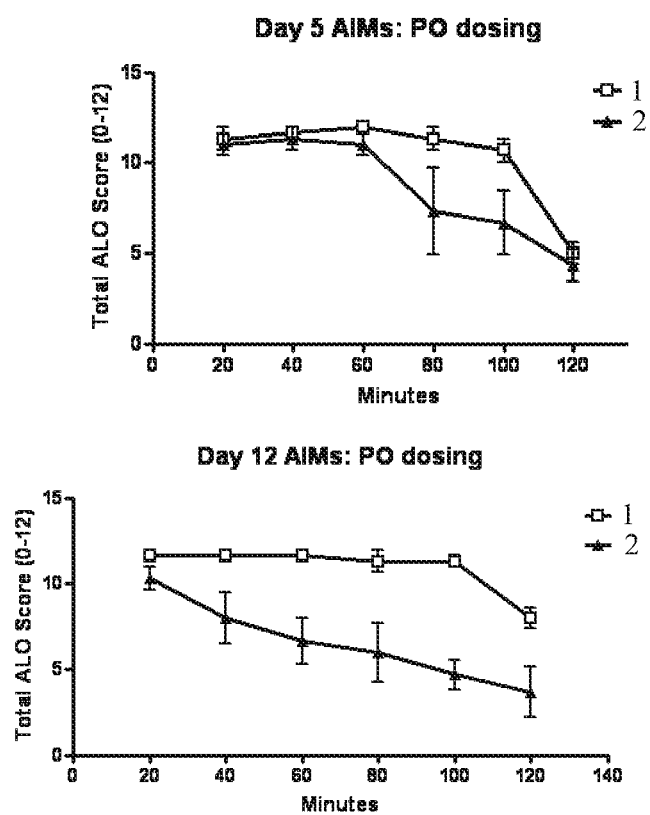
FIG. 8 shows assessment of efficacy via oral dosing of Sydnocarb in L-dopa induced dyskinesia in 6-OHDA treated rats.

Assessment of Efficacy Via Oral Dosing of Sydnocarb in L-Dopa Induced Dyskinesia in 6-OHDA Treated Rats Sprague-Dawley rats (10/group) were injected unilaterally with 6-OHDA as described herein. Two weeks later, rats were tested for amphetamine-induced rotation activity to verify the dopaminergic lesion. After an additional one week, baseline AIMs were measured and rats were treated with L-dopa at 12 mg/kg and Sydnocarb at 10 and 30 mg/kg (po) for 12 days. Drug was formulated in 0.5% methylcellulose/0.2% Tween-80. On days 5 and 12, AIMs were scored every 20 minutes for 2 hours and graphed as a sum of axial, limb, and orolingual (ALO) abnormal movements (FIG. 8). Treatment with this dose of L-dopa produced an increase in AIMS compared to baseline. Treatment with Sydnocarb via oral dose produced a decrease in AIMs compared to vehicle.

Example 8: Enhancement of L-Dopa-Mediated Anti-Akinesia: Chronic Dosing

The effects of Sydnocarb on motor function in the forelimb adjusting step (FAS) test in unilaterally lesioned 6-OHDA rats that were treated with L-dopa with and without Sydnocarb for 2 weeks were studied.

Drug Treatment

L-dopa was administered at a dose level of 6 mg/kg (ip) along with benserazide (ip; 2 mg/kg). Sydnocarb (10 or 30 mg/kg, ip) or vehicle was administered 30 minutes prior to L-dopa/benserazide. As a "priming" step, L-dopa was administered daily by itself for 1 week after the amphetamine rotation wash-out period. Subsequently, Sydnocarb, along with L-dopa, was dosed daily for an additional 12 days. For these 6 mg/kg L-dopa studies, rats were combined from two previous L-dopa/Sydnocarb studies and allowed a 3-week wash out period.

Assessment of L-Dopa Induced Motor Effects in 6-OHDA Treated Rats

Figure 9:
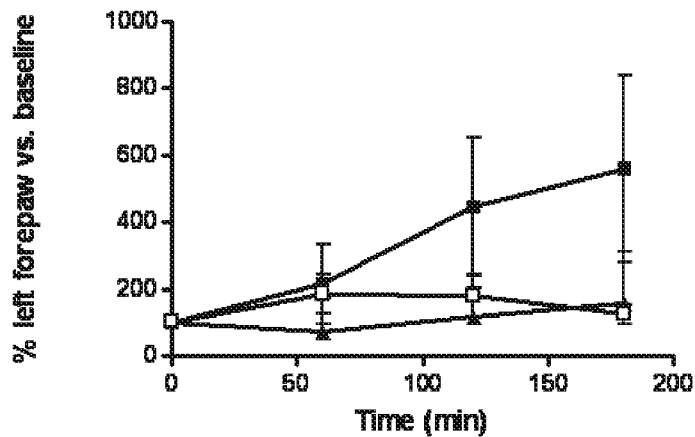
FIG. 9 shows the effects of Sydnocarb on motor function in the forelimb adjusting step test in unilaterally lesioned 6-OHDA rats that were treated with L-dopa with and without Sydnocarb for 2 weeks.
Figure 9:
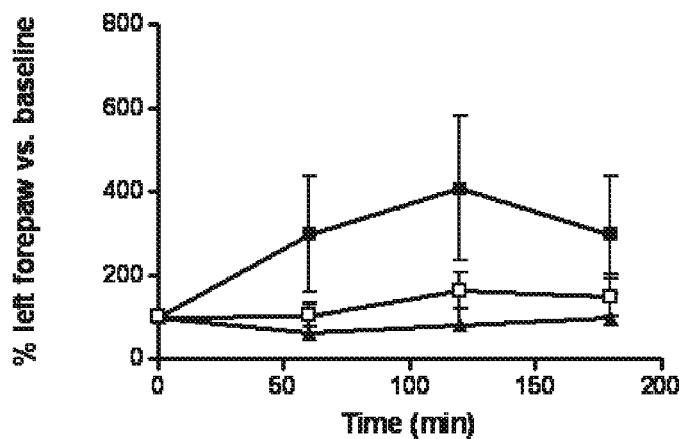

Sprague-Dawley rats (10/group) were injected unilaterally with 6-OHDA as described herein. Two weeks later, rats were tested for amphetamine-induced rotation activity to verify the dopaminergic lesion. After an additional one week, baseline FAS was measured and rats were treated with L-dopa at 6 mg/kg and Sydnocarb at 3 and 10 mg/kg (ip) for 12 days. On days 5 and 12, FAS was scored once per hour for 3 hours and graphed as a % affected paw compared to baseline (FIG. 9). Treatment with this dose of L-dopa produced a slight increase in adjusting steps compared to baseline. Treatment with 3 mg/kg Sydnocarb produced an increase in adjusting steps compared to vehicle.

Example 9: Enhancement of L-Dopa-Mediated Anti-Akinesia: Oral Dosing

The ability of Sydnocarb to be orally active was determined by examining the effects of Sydnocarb on motor function in the forelimb adjusting step (FAS) test in unilaterally lesioned 6-OHDA rats that were treated with L-dopa.

Drug Treatment

L-dopa was administered at a dose level of 6 mg/kg (ip) along with benserazide (ip; 2 mg/kg). Sydnocarb (10 mg/kg, po) or vehicle was administered 30 minutes prior to L-dopa/benserazide. As a "priming" step, L-dopa was administered daily by itself for 1 week after the amphetamine rotation wash-out period. Subsequently, Sydnocarb, along with L-dopa, was dosed daily for an additional 12 days.

Assessment of L-Dopa Induced Motor Effects in 6-OHDA Treated Rats

Figure 10:
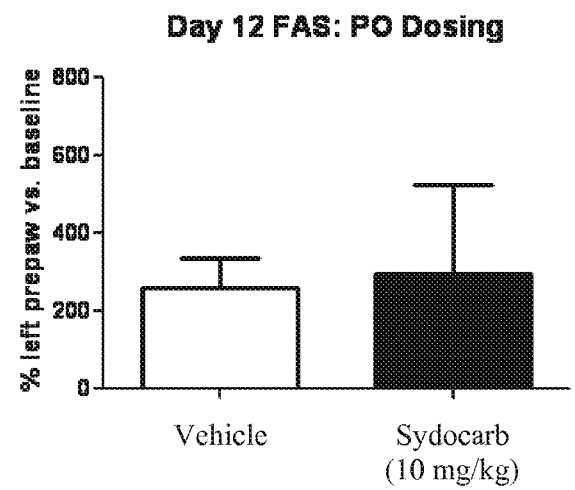
FIG. 10 shows the effects of oral dosing of Sydnocarb on motor function in the forelimb adjusting step test in unilaterally lesioned 6-OHDA rats that were treated with L-dopa.

Sprague-Dawley rats (3/group) were injected unilaterally with 6-OHDA as described herein. Two weeks later, rats were tested for amphetamine-induced rotation activity to verify the dopaminergic lesion. After an additional one week, baseline FAS was measured and rats were treated with L-dopa at 6 mg/kg and Sydnocarb at 10 mg/kg (po) for 12 days. On day 12, FAS was scored at 60 minutes post-dose and graphed as a % affected paw compared to baseline (FIG. 10). Oral treatment with 10 mg/kg Sydnocarb produced a slight increase, and importantly no decrease, in adjusting steps compared to vehicle (L-dopa alone).

Example 10: Treatment with Sydnocarb by Itself does not Cause Motor or Functional Deficits in 6-OHDA-Lesioned Rats The effects of Sydnocarb on abnormal involuntary movements (AIMs) in unilaterally lesioned 6-OHDA rats that were not treated with L-dopa were studied.

Drug Treatment

Sydnocarb was administered at 3 mg/kg (ip) to 6-OHDA-lesioned rats once per day for 12 days.

Evaluation of Dyskinesia after Treatment with Sydnocarb in 6-OHDA Lesioned Rats

Figure 11:
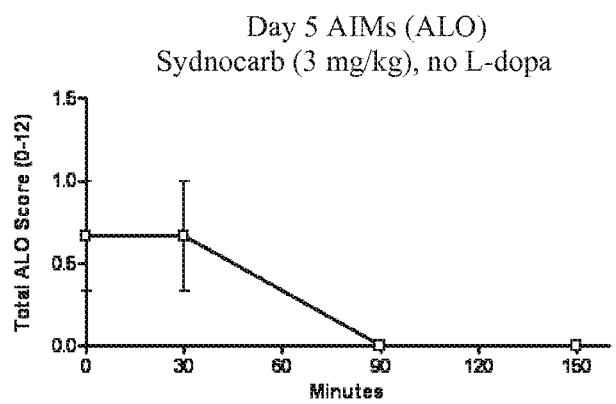
FIG. 11 shows the effects of Sydnocarb on abnormal involuntary movements in unilaterally lesioned 6-OHDA rats that were not treated with L-dopa.
Figure 11:
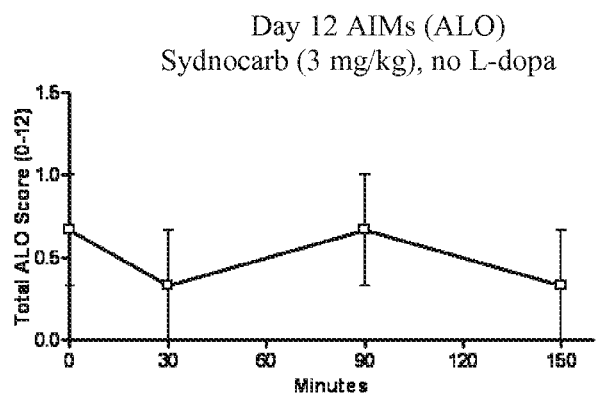

Sprague-Dawley rats (3/group) were injected unilaterally with 6-OHDA as described herein. Two weeks later, rats were tested for amphetamine-induced rotation activity to verify the dopaminergic lesion. After an additional six weeks, baseline AIMs were measured and rats were treated with Sydnocarb at 3 mg/kg (ip) for 12 days. No L-dopa was administered in this experiment. On days 5 and 12, AIMs were scored at 30, 90, and 150 minutes post-dose and graphed as a sum of axial, limb, and orolingual (ALO) abnormal movements (FIG. 11). Treatment with Sydnocarb alone produced nominal AIMs, with scores approximately 20 times lower than with L-dopa treatment.

The present disclosure is not to be limited in scope by the specific embodiments disclosed in the examples which are intended as illustrations of some aspects of the disclosure and any embodiments which are functionally equivalent are within the scope of this disclosure. Indeed, various modifications of the disclosure in addition to those shown and described herein will become apparent to those skilled in the art and are intended to fall within the appended claims.

A number of references have been cited, the entire disclosures of which are incorporated herein by reference.

What is claimed is:

1. A composition comprising sydnocarb and an anti-Parkinsonian agent, wherein the anti-Parkinsonian agent is a dopamine agonist, an anti-cholinergic, a monoamine oxidase (MAO) inhibitor, or a catechol-O-methyltransferase (COMT) inhibitor, wherein sydnocarb is not combined with an anti-epileptic agent.

2. The composition of claim 1, wherein the anti-Parkinsonian agent is a dopamine agonist.

3. The composition of claim 2, wherein the dopamine agonist is apomorphine, bromocriptine, cabergoline, lisuride, pergolide, ropinirole, pramipexole, or rotigotine.

4. The composition of claim 1, wherein the anti-Parkinsonian agent is an anti-cholinergic.

5. The composition of claim 4, wherein the anti-cholinergic is trihyexyphenidyl or benzatropine.

6. The composition of claim 1, wherein the anti-Parkinsonian agent is a monoamine oxidase (MAO) inhibitor.

7. The composition of claim 6, wherein the MAO inhibitor is selegiline or ginko biloba.

8. The composition of claim 1, wherein the anti-Parkinsonian agent is a catechol-O-methyltransferase (COMT) inhibitor.

9. The composition of claim 8, wherein the COMT inhibitor is tolcapone or entacapone.

* * * * *